(12) United States Patent
Ledee et al.

(10) Patent No.: US 10,450,561 B2
(45) Date of Patent: Oct. 22, 2019

(54) METHOD FOR INCREASING IMPLANTATION SUCCESS IN ASSISTED FERTILIZATION

(71) Applicant: MATRICELAB INNOVE, Paris (FR)

(72) Inventors: Nathalie Ledee, Paris (FR); Marie Petitbarat, Massy (FR)

(73) Assignee: MATRICELAB INNOVE, Paris (FR)

( * ) Notice: Subject to any disclaimer, the term of this patent is extended or adjusted under 35 U.S.C. 154(b) by 0 days.

(21) Appl. No.: 14/415,987

(22) PCT Filed: Jul. 19, 2013

(86) PCT No.: PCT/EP2013/065355
§ 371 (c)(1),
(2) Date: Jan. 20, 2015

(87) PCT Pub. No.: WO2014/013079
PCT Pub. Date: Jan. 23, 2014

(65) Prior Publication Data
US 2015/0184152 A1   Jul. 2, 2015

(30) Foreign Application Priority Data
Jul. 20, 2012   (EP) .................................... 12177377

(51) Int. Cl.
| G01N 33/68 | (2006.01) |
| C12Q 1/6876 | (2018.01) |
| G16H 50/30 | (2018.01) |
| C12N 15/10 | (2006.01) |

(52) U.S. Cl.
CPC ....... *C12N 15/1089* (2013.01); *C12Q 1/6876* (2013.01); *G01N 33/689* (2013.01); *C12Q 2600/158* (2013.01); *G01N 2800/367* (2013.01); *G16H 50/30* (2018.01)

(58) Field of Classification Search
CPC ............ G01N 33/689; G01N 2800/367; G06F 19/3431; C12Q 1/6876; C12Q 2600/158
See application file for complete search history.

(56) References Cited

U.S. PATENT DOCUMENTS

| 7,175,990 B2 | 2/2007 | Fisher et al. |
| 2010/0036192 A1* | 2/2010 | Yao ..................... C12Q 1/6809 600/33 |
| 2012/0016184 A1 | 1/2012 | Yao |
| 2013/0144114 A1 | 6/2013 | Simon Valles et al. |

FOREIGN PATENT DOCUMENTS

| EP | 2348318 | 7/2011 |
| WO | 2010-010213 | 1/2010 |
| WO | 2011-000805 | 1/2011 |
| WO | 2011147976 A1 | 12/2011 |

OTHER PUBLICATIONS

Lédée-Bataille et al. Role of the endometrial tripod interleukin-18, -12 and -12 in inadequate uterine receptivity in patients with a history of repeated in vitro feritlization-embryo transfer failure. Fertility and Sterility®, vol. 83, No. 3, pp. 598-605, Mar. 2005.*
Petracco et al. Global gene expression profiling of proliferative phase endometrium reveals distinct functional subdivisions. Reproductive Sciences, vol. 19, No. 10, pp. 1138-1145, May 22, 2012. (Year: 2012).*
Fassbender et al. Combined mRNA microarray and proteomic analysis of eutopic endometrium of women with and without endometriosis. Human Reproduction, vol. 27, No. 7, pp. 2020-2029, May 3, 2012. (Year: 2012).*
Krieg et al. Global alteration in gene expression profiles of deciduas from women with idiopathic recurrent pregnancy loss. Molecular Human Reproduction, vol. 18, No. 9, pp. 442-450, Apr. 14, 2012. (Year: 2012).*
Affymetrix® Data Sheet for GeneChip® 1.0 ST Array System for Human, Mouse and Rat, printed as pp. 1/8-8/8, 2007. (Year: 2007).*
Pusztai and Hess. Clinical trial design for microarray predictive marker discovery and assessment. Annals of Oncology, vol. 15, pp. 1731-1737, 2004. (Year: 2004).*
Laird et al. Endometrial CD56+ cells and implantation failure after IVF. Placenta, vol. 26, p. A26, Abstract P6.02, 2005. (Year: 2005).*
International Search Report, dated Nov. 8, 2013; Application No. PCT/EP2013/065355.
Ledee N. et al.: "New pre-conception immune biomarkers for clinical practice: interleukin-18, interleukin-15 and TWEAK on the endometrial side, G-CSF on the follicular side",J. Reprod. Immunol., vol. 88, No. 2, Mar. 2011, pp. 118-123.
Petitbarat M. et al.: "Tumor necrosis factor-like weak inducer of apoptosis (TWEAK)/fibroblast growth factor inducible-14 might regulate the effects of interleukin 18 and 15 in the human endometrium", Fertil. Steril., vol. 94, No. 3, Aug. 2010, pp. 1141-1143.
Vandermolen D.T. et al.: Human endometrial expression of granulocyte colony-stimulating factor (G-CSF) and its receptor, stimulation of endometrial G-CSF production by interleukin-lb, and G-CSF inhibition of choriocarcinoma cell proliferation 11, Am. J. Reprod. Immunol., vol. 36, No. 5, 1996, pp. 278-284.

\* cited by examiner

*Primary Examiner* — Jennifer Dunston
(74) *Attorney, Agent, or Firm* — Young & Thompson

(57) ABSTRACT

The present invention relates to a method for determining an uterine receptivity profile in order to increase implantation success in assisted fertilization.

7 Claims, 5 Drawing Sheets
Specification includes a Sequence Listing.

METHOD FOR INCREASING IMPLANTATION SUCCESS IN ASSISTED FERTILIZATION

FIELD OF INVENTION

The present invention relates to a method for determining the uterine receptivity profile during uterine implantation window in a female subject, thereby determining a personalized treatment for said subject to increase implantation success.

BACKGROUND OF INVENTION

Assisted fertilization, such as in vitro fertilization (IVF), has been used in human subjects with infertility problems successfully for three decades. Despite extensive research, it is still a difficult and expensive procedure. Indeed, less than 5% of oocytes collected and only 20-25% of embryos transferred lead to a birth. Optimization of embryo competence as well as corresponding uterine receptivity is an absolute requirement to improve success in assisted reproductive technology (ART). The success of implantation involves a synchronized crosstalk between a receptive endometrium and a functional blastocyst. This phenomenon can only take place during the window of implantation, a self-limited period of endometrial receptivity spanning between days 19 and 23 of the menstrual cycle (women). In normal menstrual cycles this is achieved through the local effects of ovarian estrogens and progesterone, which induce a series of cellular and molecular events in the endometrium leading to appropriate endometrial receptivity.

Methods for determining endometrial receptivity have been disclosed in the art: for example, U.S. Pat. No. 7,175,990 disclosed a method based on the determination of L-selectin level produced by uterine epithelial cells, wherein an increase in the L-selectin level compared to a control level indicates an increased probability of success of implantation. Another method for determining endometrial receptivity disclosed in EP2348318 is based on the determination of prostaglandin E2 or F2 alpha level in endometrial fluid. Other emerging approach like the Endometrial Receptive array (ERA system) explored 238 genes specifically expressed during the implantation window (PCT/ES2009/000386). These methods are only useful for determining endometrial receptivity to embryo implantation.

However, in case of determination of inappropriate receptivity of the endometrium, these methods are unhelpful for restoring art endometrial receptivity.

The inventors have made the observation that the inappropriate receptivity of an endometrium can be explained by two different states: an under-activated state or an over-activated state. Determining an endometrial state thus allow explaining its non-receptivity, thereby leading to adapted and personalized treatment for restoring a receptivity state.

Consequently, it is of interest to provide a method allowing the determination of an endometrial state of a female subject, this information being useful to optimize her treatment for restoring an endometrial receptivity.

SUMMARY

One object of the invention is a method for determining in a female subject the uterine receptivity profile during uterine implantation window, comprising:
determining on an endometrial sample the endometrial state by measuring:
a) biomarkers of the activity state of uterine NK (uNK) cells, and
b) biomarkers of the recruitment and maturation state of uterine NK cells,
comparing said values to reference values,
thereby determining an endometrial state which is indicative of an appropriate or inappropriate uterine receptivity.

In one embodiment, the uNK cells activity state is determined by measuring at least one of IL-18, IL-6, and IL-12 expression.

In another embodiment, the uNK cells activity state is determined by measuring IL-18 and Tweak expression and calculating an IL-18/Tweak ratio.

In another embodiment, the uNK cells recruitment is determined by quantification of the number of CD56+ uNK cells or by measuring CD56 expression.

In another embodiment, the uNK cells maturation, state is determined by measuring IL-15 expression.

In another embodiment, the uNK cells maturation state is determined by measuring IL-15 and Fn14 expression and calculating an IL-15/Fn14 ratio.

In another embodiment, the reference values are obtained from a fertile female subject.

Another object of the invention is a uterine receptivity profile based on the quantification of biomarkers specific of a) the activity state of uNK cells, and b) the recruitment and maturation state of uNK cells.

In one embodiment, the uterine receptivity profile is based on the expression of a at least one of IL-18, IL-6 and IL-12, and b) CD56 and IL-15.

In another embodiment, the uterine receptivity profile obtained by the method as described here above.

Another object of the invention is a method for increasing the success rate of an assisted reproduction technology (ART) procedure in a female subject, comprising:
determining the uterine receptivity profile of said subject during uterine implantation window as described here above, and
determining a personalized recommendation for said subject depending on the uterine receptivity profile observed.

Another object of the invention is a method for evaluating a female subject for an assisted reproduction technology (ART) procedure, comprising:
  obtaining items of information from the female subject to provide a profile for said female subject, wherein each item of information relates to preselected subject variables, wherein one of said variables is the uterine receptivity profile as described here above,
  comparing said profile for said female subject to a library of known profile patterns known to be indicative of responsiveness to an assisted reproduction technology procedure using an algorithm based upon said preselected subject variables,
  wherein said comparing provides an evaluation of said female subject tar an ART procedure.

In one embodiment, said preselected subject variables comprises histological datation (receptivity window determination); endometrium characteristics (such as endometrial thickness, endometrial volume, endometrial vascularization, uterine artery dopplers); age; infertility etiology; infertility data such as summary of the previous history and number and quality of transferred embryos; hormonal evaluation of ovarian reserve (AMH, FSH, Antral follicle count); type of ART (IVF, ICSI, IMSI, insemination).

Another object of the invention is a system for analysis of data in evaluating a female subject for an assisted reproduction technology procedure, comprising:

a computing environment, an input device, connected to a computing environment, to receive data from a user, wherein the data received comprises items of information from a female subject to provide a profile for said female subject, wherein each item of information relates to preselected subject variables, wherein one of said variables is the uterine receptivity profile as defined here above, an output device, connected to the computing environment, to provide information to the user, and a computer readable storage medium having stored thereon at least one algorithm to provide for comparing the profile for the female subject to a library of known profile patterns known to be indicative of responsiveness to an assisted reproduction technology procedure, wherein the system provides results that can be used for generation of a report providing an analysis of data in evaluating a female subject for an assisted reproduction technology procedure.

In one embodiment, said preselected subject variables comprises histological datation (receptivity window determination); endometrium characteristics (such as endometrial thickness, endometrial volume, endometrial vascularization, uterine artery dopplers); age; infertility etiology; infertility data such as summary of the previous history and number and quality of transferred embryos; hormonal evaluation of ovarian reserve (AMR, FSH, Antral follicle count); type of ART (IVF, ICSI, IMSI, insemination).

Another object of the invention is a kit for implementing the method as defined here above, comprising:

reagents for measuring expression of at least one of IL-18, IL-6, IL-12, and expression of IL-15 and CD56, optionally reagents for measuring expression of Tweak and Fn-14, optionally reagents for measuring expression of GCSF-R, optionally reagents for measuring expression of reference genes, and instructions for carrying out the method as defined here above.

Definitions

In the present invention, the following terms have the following meanings:

The term "assisted reproduction" refers to clinical and laboratory techniques used to enhance fertility in human or animals, including, but not limited to, in vitro fertilization (IVF), frozen embryo transfer (FET), intracytoplasmic sperm injection (ICSI), intra cytoplasmic morphologically selected sperm injection (IMSI), gamete intrafallopian tube transfer (GIFT), intrauterine insemination (IUI) and zygote intrafallopian tube transfer (ZIFT).

The term "implantation failure" refers to the failure of few embryos produced by assisted reproduction or through artificial insemination to implant or to implant normally in the uterus of a recipient subject. Examples of embryo implantation failure cases include, but are not limited to, implantation failure after 8 embryo transfers, implantation failure after 4 embryo transfers, implantation failure after 2 embryo transfers at J5, or implantation failure after the transfer of 2 embryos after exogenous oocyte donation. In one embodiment, the minimum of embryos transferred with subsequent a implantation failures to define an implantation failure is at least four embryos on Day-2 or -3 with an optimal morphology, six embryos on Day-2 or 3 with a medium morphology or 2 embryos on Day-5.

The term "ovarian insufficiency" refers to the loss of function of the ovaries in female younger than 40 years. Subjects affected by this disorder present also physiological rejection of the embryo. These disorders include but are not limited to: Premature Ovarian Failure, hypergonadotropic hypogonadism, gonadal dysgenesis, premature menopause, or early menopause.

The term "uterine implantation window" refers to very short period beginning about 4 to 0.5 days after ovulation and lasting about 4 days. This window defined as the implantation window defines the period in the menstrual cycle of uterine receptivity to the embryo. During the mild luteal phase, uterine remodelling events required for a successful pregnancy begin before implantation with the decidualisation of the endometrium, which occur even in the absence of a fertilized conceptus in human.

The term "subject" refers to a mammal, preferably a female mammal, more preferably a female human. In one embodiment, the subject refers to a female that underwent implantation failures. In another embodiment, the subject refers to a female that is affected by ovarian insufficiency.

The term "reference value" as used herein broadly encompasses any suitable value which may be used as a basis for comparison with respect to the measured variable. Preferably, the reference value is obtained from a fertile female subject.

The term "expression" refers interchangeably to expression of a gene including transcripts of the gene, mRNA, polypeptide translation products of such RNA transcripts whether or not such product is modified post transcriptionally, or expression of gene product, including the encoded polypeptide or protein. Expression of a gene product may be determined, for example, by immunoassay using one or more antibody(ies) that bind with the polypeptide. Alternatively, expression of a gene may be determined by measurement of mRNA levels, for example, by RT-PCR, qPCR.

The term "normalized level" refers to an expression level of a gene relative to an expression level of a reference gene.

DETAILED DESCRIPTION

As shown in the Examples, when only using the determination of one of (1) the activity state of uterine NK cells or of cytokine endometrial environment, (2) the maturation state of uterine NK cells or (3) the recruitment state of uterine NK cells, more than 40% of the tested women are classified as presenting a normal endometrial state or an appropriate uterine receptivity profile.

When implementing the method of the invention, the Inventors have discovered that among the 42% of subjects classified as presenting a normal endometrium as determined by only using the determination of the activity state of uterine NK cells or cytokine endometrial environment, almost 25% do not in fact present a normal endometrial state.

In addition, among the 43% of subjects classified as presenting a normal endometrium as determined by only using the determination of the maturation state of uterine NK cells, almost 75% do not in fact present a normal endometrial state.

Furthermore, among the 47% of subjects classified as presenting a normal endometrium as determined by only using the determination of the recruitment state of uterine NK cells, 80% do not present in fact a normal endometrial state.

There is thus a need for a method that allows a more accurate determination of the endometrial state, thereby allowing the women who would have been considered as "normal" to benefit from a personalized and optimized treatment for restoring an uterine receptivity and thus increase their chance of having an evolutive pregnancy or live birth.

The present invention aims to determine the uterine/endometrium receptivity by determining the endometrial state, in order to optimize a treatment for restoring an uterine receptivity.

One object of the invention is a method for determining in a female subject an uterine receptivity profile during uterine implantation window, comprising:
determining, on an endometrial sample the endometrial state by measuring:
- a) biomarkers of the activity state of uterine natural killer (uNK) cells or of the cytokine endometrial environment, and
- b) biomarkers of the recruitment and maturation state of uterine NK comparing said values to reference values, thereby determining an endometrial state which is indicative of an appropriate or inappropriate uterine receptivity.

Discriminating the endometrial state of a subject in three particular states: (1) under-activated state, (2) normal state and (3) over-activated state, allows the classification of the subject into two categories: appropriate uterine receptivity (normal endometrial state) and inappropriate uterine receptivity, the latter being divided into two subcategories: absence of receptivity (under-activated endometrial state) and abnormal receptivity (over-activated endometrial state).

Discriminating subjects into these three categories thus allow the monitoring of their treatment in order to restore an appropriate endometrial receptivity, thereby increasing the success rate and optimizing the ART procedure.

Therefore an object of the invention is a method for determining in a female subject an uterine receptivity profile during uterine implantation window, comprising:
determining on an endometrial sample the endometrial state by measuring:
- a) biomarkers of the activity state of uterine natural killer (uNK) cells or of the cytokine endometrial environment,
- b) biomarkers of the recruitment and maturation state of uterine NK cells, and
- c) comparing said values to reference values, thereby discriminating the endometrial state of a subject in three particular states: (1) under-activated state, (2) normal state and (3) over-activated state, which allows the classification of the subject into two categories: appropriate uterine receptivity (normal endometrial state) and inappropriate uterine receptivity, the latter being divided into two subcategories: absence of receptivity (under-activated endometrial state) and abnormal receptivity (over-activated endometrial state).

In one embodiment, said endometrial sample is an endometrial biopsy.

As used herein, the uNK cells activity status refers to the external uNK cells activity status on surrounding endometrial cells.

As used herein, the cytokine endometrial environment activity status refers to the immune cells activity status on surrounding endometrial cells.

In one embodiment of the invention, the uNK cells activity status or the cytokine endometrial environment activity status is determined by measuring the expression level of at least one of the following biomarkers IL-18, IL-6 and IL-12.

In one embodiment, the expression level of IL-18, IL-6 or IL-12 may be measured by assessing the quantity of protein, or of nucleic acid corresponding to the gene encoding IL-18, IL-6 or IL-12 (such as, for example, the quantity of RNA). In one embodiment, said level may be normalized to the level of a product of reference genes such as for example RPL-13A, beta-2 microgobulin or tatabox protein TBP. In another embodiment, said level may be normalized to the geometric mean level of at least two products of reference genes. In another embodiment, said reference genes are not actin and GAPDH.

As used herein, the term "IL-6" refers to Interleukine 6; the term "IL-12" refers to Interleukine 12 and the term IL-18 refers to interleukine 18.

Methods for measuring the expression level of IL-6, IL-12 or IL-18 in a sample are well known from the skilled artisan, and include, but are not limited to, bioassays, such as, for example, ELISA, Luminex method (such as, for example, Luminex method using the detection kit from Biorad (Bioplex pro Human cytokines), RT-PCR, RT-qPCR, PCR, qPCR, real-time PCR, real-time qPCR, DNA Chip, and the like; and immunoassays, such as, for example, FloCytomix Technology (Biosource) or BD Cytometric Beads Array (BD Bioscience).

In another embodiment of the invention, the uNK cells activity status or the cytokine endometrial environment activity status is determined by measuring the expression level of the biomarkers IL-18 and Tweak and calculating an IL-18/Tweak ratio.

As used herein, the term "Tweak" refers to a protein encoded by the TNFSF12 gene. Methods for measuring the expression level of Tweak in a sample are well known from the skilled artisan, and include, but are not limited to, bioassays, such as, for example, ELISA, RT-PCR, RT-qPCR, PCR, qPCR, real-time PCR, real-time qPCR, DNA Chip, and the like; and immunoassays, such as, for example, FloCytomix Technology (Biosource) or BD Cytometric Beads Array (BD Bioscience).

In one embodiment of the invention, the uNK cells recruitment is determined by quantification of the number of uNK cells.

The number of uNK cells can be quantified by determining the number of CD56+ uterine cells. Determining said number may be carried out by either using immunohistochemistry of frozen or paraffin fixed sections with antibodies anti-CD56 to identify NK cells staining. In one embodiment, the CD56+ cells are counted in a 40× field. In another embodiment, the CD56+ cells are counted in four 40× fields and then the mean number is calculated.

In another embodiment of the invention, the uNK cells recruitment is determined by measuring the expression level of CD56.

In one embodiment of the invention, measuring the expression level of CD56 is optional.

Methods for measuring the expression level of CD56 in a sample are well known from the skilled artisan, and include, but are not limited to, bioassays, such as, for example, ELISA, RT-PCR, RT-qPCR, PCR, qPCR, real-time PCR, real-time qPCR, DNA Chip, and the like; and immunoassays, such as, for example, FloCytomix Technology (Biosource) or BD Cytometric Beads Array (BD Bioscience).

As used herein, the term "CD56+ cells" refers to cells expressing CD56, also named NCAM (neural cell adhesion molecule).

In one embodiment of the invention, the uNK cells maturation state is determined by measuring the expression level of the following biomarker: IL-15.

In one embodiment, the expression level of IL-15 may be measured by assessing the quantity of protein, or of nucleic acid corresponding to the gene encoding IL-15 (such as, for example, the quantity of RNA). In one embodiment, said level may be normalized to the level of a product of reference genes such as for example RPL-13A, beta-2 microglobulin or tatbox protein TBP. In another embodiment, said level may be normalized to the geometric mean level of at least two products of reference genes. In another embodiment, said reference genes are not actin and GAPDH.

As used herein, the term "IL-15" refers to Interleukin 15.

Methods for measuring the expression level of IL-15 in a sample are well known from the skilled artisan, and include, but are not limited to, bioassays, such as, for example, ELISA, Luminex method (such as, for example, Luminex method using the detection kit from Biorad (Bioplex pro Human cytokines), RT-PCR, RT-qPCR, PCR, qPCR, real-time PCR, real-tune qPCR, DNA Chip, and the like; and immunoassays, such as, for example, FloCytomix Technology (Biosource) or BD Cytometric Beads Array (BD Bioscience).

In another embodiment of the invention, the uNK cells maturation state is determined by measuring the expression level of the following biomarkers: IL-15 and Fn-14 and calculating an IL-15/Fn14 ratio.

As used herein, the term "Fn14" refers to the fibroblast growth factor inducible-14, which is a receptor for Tweak.

Methods for measuring the expression level of Fn-14 in a sample are well known from the skilled artisan, and include, but are not limited to, bioassays, such as, for example, ELISA, Luminex method, RT-PCR, RT-qPCR, PCR, qPCR, real-time PCR, real-time qPCR, DNA Chip, and the like; and immunoassays, such as, for example, FloCytomix Technology (Biosource) or BD Cytometric Beads Array (BD Bioscience).

In one embodiment, a reference value can be relative to a number or value derived from population studies, including without limitation, such subjects having similar age range, subjects in the same or similar ethnic group or subjects being in embryo implantation failure or subjects undergoing ovarian insufficiency.

One object of the invention is a method for determining in a female subject a uterine receptivity profile during uterine implantation window, comprising:
determining on an endometrial sample the endometrial state by
  a) measuring: biomarkers of the activity state of uterine natural killer (uNK) cells or the cytokine endometrial environment, and biomarkers of the recruitment and maturation state of uterine NK cells,
  b) classifying the endometrial state based on the determination of IL-18/Tweak ratio by comparing said value to reference value,
  c) if the endometrial state is classified as normal in step b), classifying the endometrial state based on the determination of IL-15/Fn14 ratio and optionally the determination of CD56, by comparing said values to reference values, thereby determining an endometrial state which is indicative of an appropriate or inappropriate uterine receptivity.

As shown in the Examples, if IL15/Fn14 ratio is considered first for classifying the endometrial state, the diagnostic is inappropriate in 14% of the cases.

In one embodiment of the invention, a reference value can be derived from the measurement of the level of the following biomarkers: IL-18, IL-6, IL-12, IL-15, G-CSF receptor or the calculation of IL-18/Tweak ratio or IL-15/Fn-14 ratio or the determination of the number of uNK cells in at least one control sample derived from one or more subjects substantially healthy. As used herein, a "substantially healthy subject" refers to a subject who has not experienced an implantation failure or a subject who is considered as a fertile subject or a subject having a normal endometrial state.

In another embodiment of the invention, a reference value can be derived from the measurement of the level of the following biomarkers: IL-18, IL-6, IL-12, IL-15, G-CSF receptor or the calculation of IL-18/Tweak ratio or IL-15/Fn-14 ratio or the determination of the number of uNK cells in at least one control sample derived from one or more subjects having an under-activated or over-activated endometrial state.

In one embodiment of the invention, the method of the invention comprises the following steps:
  a) classification of the endometrial state based on the determination of uNK cells or the cytokine endometrial environment activity state value,
  b) if the endometrial state cannot be classified as under-activated or over-activated in a), classification of the endometrial state based on the determination of the uNK cells recruitment.
  c) if the endometrial state cannot be classified as under-activated or over-activated in b), classification of the endometrial state based on the combination of the values obtained for the uNK cells recruitment and the uNK cells maturation state.

One object of the invention is a method for determining in a female subject a uterine receptivity profile during uterine implantation window, comprising:
determining on an endometrial sample the endometrial state by:
  a) measuring biomarkers of the activity state of uterine natural killer (uNK) cells or the cytokine endometrial environment,
  b) classifying the endometrial state as under-activated or overactivated by comparing said values to reference values,
  c) if the endometrial state cannot be classified as under-activated or overactivated in b), measuring biomarkers of the recruitment and/or maturation state of uterine NK cells.
  d) classifying the endometrial state based on the determination of the uNK cells recruitment and/or maturation by comparing said values to reference values.

In another embodiment of the invention, the method of the invention comprises the following steps:
  a) classification of the endometrial state based on the determination of the IL-18/Tweak ratio value,
  b) if the endometrial state cannot be classified as under-activated or over-activated in a), classification of the endometrial state based on the determination of the number of CD56+ uNK cells or of the CD56 expression level,
  c) if the endometrial state cannot be classified as under-activated or over-activated in b), classification of the endometrial state based on the combination of the values obtained for the number of CD56+ uNK cells or for the CD56 expression level and the IL-15/Fn-14 ratio value.

In another embodiment of the invention, the method of the invention comprises the allowing steps:
a) measuring the IL-18/Tweak ratio value as biomarker of the activity state of uterine natural killer (uNK) cells or the cytokine endometrial environment,
b) classifying the endometrial state as under-activated or overactivated by comparing said value to a reference value,
c) if the endometrial state cannot be classified as under-activated or overactivated in b), measuring the IL-15/Fn-14 ratio value as biomarker of the recruitment and/or maturation state of uterine NK cells,
d) classifying the endometrial state as under-activated or over-activated by comparing said value to a reference value.

In another embodiment of the invention, the method of the invention comprises the following steps:
a) classification of the endometrial state based on the determination of a uNK cells maturation state value,
b) if the endometrial state cannot be classified as under-activated or over-activated in a), classification of the endometrial state based on the determination of the uNK cells recruitment,
c) if the endometrial state cannot be classified as under-activated or over-activated in b), classification of the endometrial state based on the determination of the uNK cells or the cytokine endometrial environment activity state value.

In another embodiment of the invention, the method of the invention comprises the following steps:
a) classification of the endometrial state based on the determination of the IL-15/Fn-14 ratio value,
b) if the endometrial state cannot be classified as under-activated or over-activated in a), classification of the endometrial state based on the determination of the number of CD56+ uNK cells or of the CD56 expression level,
c) if the endometrial state cannot be classified as under-activated or over-activated in b), classification of the endometrial state based on the determination of the IL-18/Tweak ratio value.

In another embodiment of the invention, the method of the invention comprises the following steps:
a) classification of the endometrial state based on the determination of a uNK cells maturation state value,
b) if the endometrial state cannot be classified as under-activated or over-activated in a), classification of the endometrial state based on the determination of the uNK cells or the cytokine endometrial environment activity state value,
c) if the endometrial state cannot be classified as under-activated or over-activated in b), classification of the endometrial state based on the determination of the uNK cells recruitment.

In another embodiment of the invention, the method of the invention comprises the following steps:
a) classification of the endometrial state based on the determination of the IL-15/Fn-14 ratio value,
b) if the endometrial state cannot be classified as under-activated or over-activated in a1, the classification of the endometrial state based on the determination of the Il-18/Tweak ratio value,
c) if the endometrial state cannot be classified as under-activated or over-activated in b), classification of the endometrial state based on the determination of the number of CD56+ uNK cells or of the CD56 expression level.

In another embodiment of the invention, the expression level of G-CSF receptor in the endometrium may also be determined.

As used herein, the term "G-CSF receptor" refers to the granulocyte-colony stimulating factor receptor.

Methods for measuring the level of G-CSF receptor in a sample are well known from the skilled artisan, and include, but are not limited to, bioassays, such as, for example, ELISA, Luminex methods, RT-PCR, RT-qPCR, PCR, qPCR, real-time PCR, qPCR, DNA Chip, and the like; and immunoassays, such as, for example, FloCytomix Technology (Biosource) or BD Cytometric Beads Array (BD Bioscience).

The determination of the level of G-CSF receptor leads to the classification of the subject into two groups: corticoid responsive and corticoid non-responsive.

In one embodiment of the invention, the methods as described here above may further comprise a step wherein the subject is classified between corticoid responsive and corticoid non responsive based on the expression of G-CSF receptor. Preferably, the subject is classified into one of these two groups when presenting an over-activated endometrium.

In one embodiment of the invention, a uNK cells or a cytokine endometrial activity state value, preferably a IL-18/Tweak ratio value, inferior to 0.5 times a uNK or a cytokine endometrial activity state reference value, preferably a IL-18/Tweak ratio reference value is indicative of an under-activated endometria state.

In another embodiment of the invention, a uNK cells or a cytokine endometrial activity state value, preferably a IL-18/Tweak ratio value, inferior to 0.45, 0.4, 0.35, 0.3, 0.25, 0.2, 0.15, 0.1 times a uNK or a cytokine endometrial activity state reference value, preferably a IL-18/Tweak ratio reference value, is indicative of an under-activated endometrial state.

In said embodiments, the reference values are obtained from a substantially healthy subject.

In one embodiment of the invention, a uNK or a cytokine endometrial activity state value, preferably a IL-18/Tweak ratio value, superior to 1.8 times a uNK activity state reference value, preferably a IL-18/Tweak ratio reference value, is indicative of an over-activated endometrial state.

In another embodiment of the invention, a uNK or a cytokine endometrial activity state value, preferably a IL-18/Tweak ratio value, superior to 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.5, 6, 6.5, 7, 7.5, 8, 8.5, 9, 9.5, 10, 10.5, 11, 11.5, 12, 13, 14, 15, 20, 25, 30, 35, 40, 45, 50, 75, 100 times a uNK or a cytokine endometrial activity state reference value, preferably a IL-18/Tweak ratio reference value, is indicative of an over-activated endometrial state.

In said embodiments, the reference values are obtained from a substantially healthy subject.

In one embodiment of the invention, a uNK or a cytokine endometrial activity state value, preferably a IL-18/Tweak ratio value, comprised from 0.5 times to 1.8 times a uNK or a cytokine endometrial activity state reference value, preferably a IL-18/Tweak ratio reference value, and a number of CD56+ uNK cells inferior to 10 per field is indicative of an under-activated endometrial state.

In said embodiment, the reference values are obtained from a substantially healthy subject.

In one embodiment of the invention, a uNK or a cytokine endometrial activity state value, preferably a IL-18/Tweak ratio value, comprised between 0.5 times and 1.8 times a uNK or a cytokine endometrial activity state reference value, preferably a IL-18/Tweak ratio reference value, and a number of CD56+ uNK cells comprised from 10 to 70 per field and a uNK cells maturation state value, preferably a IL-15/Fn-14 ratio value, inferior to 0.3 times a uNK cells maturation state reference value, preferably a IL-15/Fn-14 ratio reference value, is indicative of an under-activated endometrial state. In another embodiment of the invention, a uNK cells maturation state value, preferably a IL-15/Fn-14 ratio value, inferior to 0.25, 0.2, 0.15, 0.1 times a uNK cells maturation state reference value, preferably a IL-15/Fn-14 ratio reference value, is indicative of an under-activated endometrial state.

In said embodiments, the reference values are obtained from a substantially healthy subject.

In one embodiment of the invention, a uNK or a cytokine endometrial activity state value, preferably a IL-18/Tweak ratio value, comprised between 0.5 tunes and 1.8 times a uNK activity state reference value, preferably a IL-18/Tweak ratio reference value, and a number of CD56+ uNK cells comprised from 10 to 70 per field and a uNK cells maturation state value, preferably a IL-15/Fn-14 ratio value, superior to 2 times a uNK cells maturation state reference value, preferably a IL-15/Fn-14 ratio reference value, is indicative of an over-activated state by hyper-activation of uNK cells.

In another embodiment of the invention, a uNK cells maturation state value, preferably a IL-15/Fn-14 ratio value, superior to 2.1, 2.2, 2.3, 2.4, 2.5, 2.6, 2.7, 2.8, 2.9, 3, 3.1, 3.2, 3.3, 3.4, 3.5, 3.6, 3.7, 3.8, 7.9, 4, 4.1, 4.2, 4.3, 4.4, 4.5, 4.6, 4.7, 4.8, 4.9, 5, 5.5, 6, 6.5, 7, 7.5, 8.5, 9, 9.5, 10, 10.5, 11, 11.5, 12, 13, 14, 15, 20, 25, 30, 35, 40, 45, 50, 75, 100 times a uNK cells maturation state reference value, preferably a IL-15/Fn-14 ratio reference value, is indicative of an over-activated endometrial state.

In said embodiments, the reference values are obtained from a substantially healthy subject.

In one embodiment of the invention, a uNK or a cytokine endometrial activity state value, preferably a IL-18/Tweak ratio value, comprised between 0.5 times and 1.8 times a uNK or a cytokine endometrial activity state reference value, preferably a IL-18/Tweak ratio reference value, and a number of CD56+ uNK cells superior to 70 per field and a uNK cells maturation state value, preferably a IL-15/Fn-14 ratio value, superior to 2 times a uNK cells maturation state reference value, preferably a IL-15/Fn-14 ratio reference value, is indicative of an over-activated state by hyper-activation of uNK cells.

In another embodiment of the invention, a uNK cells maturation state value, preferably a IL-15/Fn-14 ratio value, superior to 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.5, 6, 6.5, 7, 7.5, 8, 8.5, 9, 9.5, 10, 10.5, 11, 11.5, 12, 13, 14, 15, 20, 25, 30, 35, 40, 45, 50, 75, 100 times a uNK cells maturation state reference value, preferably a IL-15/Fn-14 ratio reference value, is indicative of an over-activated endometrial state.

In said embodiments, the reference values are obtained from a substantially healthy subject.

In one embodiment of the invention, a uNK cells or a cytokine endometrial activity state value, preferably a IL-18/Tweak ratio value, inferior to 0.03 is indicative of an under-activated endometrial state.

In another embodiment of the invention, a uNK cells or a cytokine endometrial activity state value, preferably a IL-18/Tweak ratio value, inferior to 0.025, 0.02, 0.015, 0.01, 0.005 is indicative of an under-activated endometrial state.

In one embodiment of the invention, a uNK cell or a cytokine endometrial activity state value, preferably a IL-18/Tweak ratio value, superior to 0.11 is indicative of an over-activated endometrial state.

In another embodiment of the invention, a uNK cell or a cytokine endometrial activity state value, preferably a IL-18/Tweak ratio value, superior to 0.12, 0.13, 0.14, 0.15, 0.16, 0.17, 0.18, 0.19, 0.2, 0.25, 0.3, 0.35, 0.4, 0.45, 0.5, 0.55, 0.6, 0.65, 0.7, 0.75, 0.8, 0.85, 0.9, 0.95, 1, 1.1, 1.2, 1.3, 1.4, 1.5, 1.6, 1.7, 1.8, 1.9, 2, 2.5 is indicative of an under-activated endometrial state.

In one embodiment of the invention, a uNK cells recruitment value, preferably a number of CD56+ uNK cells, inferior to 10 per field is indicative of an under-activated endometrial state.

In another embodiment of the invention, a uNK cells recruitment value, preferably a number of CD56+ uNK cells, inferior to 9, 8, 7, 6, 5, 3, 2, 1 per field is indicative of an under-activated endometrial state.

In one embodiment of the invention, a uNK cells recruitment value, preferably a number of CD56+ uNK cells, comprised from 10 to 70 per field and a uNK cells maturation state value, preferably a IL-15/Fn-14 ratio value, inferior to 0.3 is indicative of an under-activated endometrial state.

In another embodiment of the invention, a uNK cells recruitment value, preferably a number of CD56+ uNK cells, comprised from 10 to 70 per field and a uNK cells maturation state value, preferably a IL-15/Fn-14 ratio value, inferior to 0.25, 0.2, 0.15, 0.1, 0.05 is indicative of an under-activated endometrial state.

In one embodiment of the invention, a uNK cells recruitment value, preferably a number of CD56+ uNK cells, comprised from 10 to 70 per field and a uNK cells maturation state value, preferably a IL-15/Fn-14 ratio value, superior to 2 is indicative of an over-activated endometrial state.

In another embodiment of the invention, a uNK cells recruitment value, preferably a number of CD56+ uNK cells, comprised from 10 to 70 per field and a uNK cells maturation state value, preferably a IL-15/Fn-14 ratio value, superior to 2.5, 3, 3.5, 4, 4.5, 5, 5.5, 6, 6.5, 7, 7.5, 8, 8.5, 9, 9.5, 10, 11, 12, 13, 14, 15, 20 is indicative of an over-activated endometrial state.

In one embodiment of the invention, a uNK cells recruitment value, preferably a number of CD56+ uNK cells, superior to 70 per field and a uNK cells maturation state value, preferably a IL-15/Fn-14 ratio value, superior to 2 is indicative of an over-activated endometrial state.

In another embodiment of the invention, a uNK cells recruitment value, preferably a number of CD56+ uNK cells, superior to 70 per field and a uNK cells maturation state value, preferably a IL-15/Fn-14 ratio value, superior to 2.5, 3, 3.5, 4, 4.5, 5, 5.5, 6, 6.5, 7, 7.5, 8, 8.5, 9, 9.5, 10, 11, 12, 13, 14, 15, 20 is indicative of an over-activated endometrial state.

In one embodiment, a G-CSF receptor value superior to 0.7 is indicative of a subject non-responsive to corticoids.

In another embodiment, a G-CSF receptor value inferior or equal to 0.7 is indicative of a subject responsiveness to corticoids.

In another embodiment, a G-CSF receptor value is not indicative of subject responsiveness to corticoids.

Another object of the invention is a profile of uterine receptivity, wherein said profile is based on a) the activity state of uterine NK (uNK) cells or cytokine endometrial environment, and b) the recruitment and maturation state of uterine NK cells, in an endometrial sample obtained during uterine implantation window.

In one embodiment, said profile of uterine receptivity is based on the expression level of at least one of IL-18, IL-6 or IL-12, preferably IL-18, and the expression level of IL-15 and CD56.

In another embodiment, said profile of uterine receptivity is based on the expression level of at least one of IL-18, IL-6 or IL-12, preferably IL-18, and the expression level of IL-1.5 and the number of CD56+ uNK cells.

In another embodiment, said profile of uterine receptivity is based on the ratio value of IL-18/Tweak and IL-15/Fn14 and the expression level of CD56.

In another embodiment, said profile of uterine receptivity is based on the ratio value of IL-18/Tweak and IL-15/Fn14 and the number of CD56+ uNK cells.

In one embodiment, said profile of uterine receptivity is based on a sequential determination of the endometrial state based first on the ratio value of IL-18/Tweak and then on the ratio value of IL-15/Fn14.

In one embodiment, said profile of uterine receptivity is obtained according to the method here above described.

In one embodiment, said profile of uterine receptivity is classified between appropriate or inappropriate (absence of receptivity or abnormal receptivity) uterine receptivity based on determination of the endometrial state (normal, under-activated or over-activated).

Another object of the invention is a method for increasing, the success rate of an assisted reproduction technology (ART) procedure in a female subject, comprising:
determining an uterine receptivity profile as described here above, and
determining a personalized recommendation for said subject depending on the uterine receptivity profile observed.

Another object of the invention is a method for increasing the success rate of an assisted reproduction technology (ART) procedure in a female subject, comprising:
determining the endometrial state of said subject during uterine implantation window as described here above, and
determining a personalized recommendation for said subject depending on the endometrial state observed.

In one embodiment of the invention wherein the endometrial state determined as described here above is an under-activated state or the uterine receptivity profile is inappropriate due to an absence of receptivity, the recommendation may be to stimulate mechanically in the luteal phase preceding the IVF cycle the endometrium by creating a local injury through an endometrial biopsy. Without willing to be bound to a theory, said local injury may induce immune cells and pro-inflammatory cytokines to prepare the soil for a future implantation through a better adhesion.

In another embodiment of the invention wherein the endometrial state determined as described here above is an under-activated state or the uterine receptivity profile is inappropriate due to an absence of receptivity, the recommendation may be to decrease the level of the hormonal stimulation to decrease the exposure of endometrial cells to high concentration of oestradiol. This means for example decreasing the number of FSH unit to trigger the ovulation in case of IVF (oestradiol level measured in the blood the day of triggering the ovulation should be lower than 1500 pg/ml) or replacing frozen embryo after thawing in monitored natural cycles (and not as usual substituted cycle by oestrogens and progesterone). Without willing to be bound to a theory, a minimal stimulation or a replacement in natural cycle will impair an aggravation of the local under-activation already present. Oestrogens will not be introduced in supplementation during the luteal phase following the embryo replacement for the same reasons.

In another embodiment of the invention wherein the endometrial state determined as described here above is an under-activated state or the uterine receptivity profile is inappropriate due to an absence of receptivity, the recommendation may be to stimulate the immune tolerance, the angiogenesis and the proliferation of uNK cells through the administration of human Chorionic Gonadotropin Hormons (HCG) during the implantation window. For example, 1500 IU of HCG may be injected 4, 6 and 8 days after the oocyte retrieval (IVF) or 6-8-10 days after the ovulation surge (replacement of frozen embryo in natural cycle). Without willing to be bound to a theory. HCG will profoundly influence immunological tolerance, angiogenesis at the maternal-fetal interface and be involved in the mobilisation of uNK cells via a mannose receptor binding. Particularly, HCG will induce VEGF production by endometrial epithelium, increase endothelial cells proliferation and migration of smooth muscle cells leading to the maturation of vessels.

In another embodiment of the invention wherein the endometrial state determined as described here above is an under-activated state or the uterine receptivity profile is inappropriate due to an absence of receptivity, sexual intercourse are recommended after embryo transfer. Without willing to be bound to a theory, seminal plasma may play a role in preparing the soil for its mission of implantation by regulating recruitment and activation of T regulatory cells.

In one embodiment of the invention wherein the endometrial state determined as described here above is an over-activated state or the uterine receptivity profile is inappropriate due to an abnormal receptivity, no local injury is recommended during the cycle preceding an embryo implantation.

In another embodiment of the invention wherein the endometrial state determined as described here above is an over-activated state or the uterine receptivity profile is inappropriate due to an abnormal receptivity, high level of ovarian stimulation is recommended in order to allow a high level of exposure of endometrial cells to oestradiol.

For example, in case of IVF, normal doses of FSH will be used to trigger the super ovulation with an objective to collect 9 to 12 oocytes (the initial dose of FSH will be between 225 to 400 IU). In case of replacement of frozen embryo, substitution by oestrogens and progesterone will be used. To enhance the local concentration of oestrogens, the vaginal route of administration is recommended (oestradiol 2 mg, 1 pill three time a day vaginally). Finally, in the luteal phase, after the embryo transfer, prescription of oestradiol may be maintained (oestradiol 2 mg, 1 pill three time a day orally or vaginally).

In another embodiment of the invention wherein the endometrial state determined as described here above is an over-activated state or the uterine receptivity profile is inappropriate due to an abnormal receptivity, high doses of progesterone are recommended after the oocyte retrieval (for example 400 mg three times a day vaginally).

In another embodiment of the invention wherein the endometrial state determined as described here above is an over-activated state or the uterine receptivity profile is inappropriate due to an abnormal receptivity, drugs aiming at controlling the pro-inflammatory local environment will be recommended from the beginning of the stimulation. The choice of the drugs depend on the determination of corticoids responsiveness based on the level of expression of the G-CSF receptor as described here above.

For example, if the subject is responsive to corticoids, corticosteroids may be administered from the first day of the cycle of the IVF cycles until the pregnancy test (an example of corticosteroid to be administered is Prednisone 20 mg from day 1 to day of pregnancy test). If the subject is non-responsive to corticoids, a combination of low dose of acetyl salicylic acid with low-weight heparins (such as Lovenox 0.4 day of oocyte retrieval-Day of pregnancy test) may be administered. Another example of treatment when the subject is non-responsive to corticoids is the use of intralipids. Intralipids have been mainly explored to control cytotoxicity of peripheral NK cells from the blood, but preliminary results suggest a control of cytotoxixity of uterine NK cells and an immunoregulation on regulatory T cells. In one embodiment, 100 ml Intralipid at 20% is dissolved in 500 cc of normal saline 7-14 days prior to embryo transfer. Preferably, the infusion time for 500 mL must not be shorter than 2 hours. The cure may be repeated with a positive pregnancy test then administered every month until the 12th week.

In another embodiment of the invention wherein the endometrial state determined as described here above is an over-activated state or the uterine receptivity profile is inappropriate due to an abnormal receptivity, a therapeutically effective amount of anti-oxidant agent is to be administered to the subject. An example of anti-oxidant agent that can be administered to the subject is TOCO 500 mg, 2 pills a day from D1 until D pregnancy test.

In another embodiment of the invention wherein the endometrial state determined as described here above is an over-activated state or the uterine receptivity profile is inappropriate due to an abnormal receptivity, no sexual intercourse is recommended after embryo transfer.

The present invention also aims at providing methods and computer-based systems for facilitating assessment of clinical infertility. The methods and systems can be implemented to facilitate assessment of a subject for an in vitro fertilization treatment or assisted reproduction technology procedure. Specifically, the methods and systems can be implemented to facilitate assessment of the uterine receptivity of a subject and subsequently provide a personalized treatment for in vitro fertilization of said subject.

In one embodiment, the method includes obtaining items of information from a female subject to provide a profile for the female subject, wherein each item of information relate to preselected subject variables, comparing the profile for the female subject to a library of known profile patterns known to be indicative of responsiveness to an in vitro fertilization procedure using an algorithm based upon the preselected subject variables, wherein the comparing provides an evaluation of the female subject for an in vitro fertilization procedure, in particular an evaluation of the female subject uterine receptivity, in order to provide a personalized treatment for in vitro fertilization of said subject. In one embodiment, one of said variables is the uterine receptivity profile as defined here above. In another embodiment, one of said variables is the endometrial state as defined here above.

In one embodiment, the items of information may be provided by the female subject based on a written or electronic questionnaire or may be requested, transcribed, or otherwise logged, by a health care practitioner, such as a doctor, nurse, technician, or the like.

Exemplary items of information relating to preselected subject variables include, but are not limited to: histological dating (to determine that the subject is in the receptivity window); subject characteristics, such as age, previous infertility history, clinical diagnosis; endometrium characteristics, such as endometrial thickness, endometrial volume, endometrial vascularization, uterine artery dopplers; etiology of the infertility, clinical treatment information, such as type of medication, number of days of stimulation, number of oocytes, etc.; conventional embryo morphology data, such as number and quality of embryos transferred, developmental stage, grade, and the like; evaluation of ovarian reserve, such as 3 days follicle stimulating hormone (FSH) level, 3 days anti-mullerian hormone (AMH) level, Antral follicule count on Day-3; body mass index, polycystic ovarian disease, spermogram with spermocytogram, unexplained female infertility, number of spontaneous miscarriages, year, other causes of female infertility, number of previous pregnancies, number of previous term deliveries, endometriosis, tubal disease, tubal ligation, male infertility, uterine fibroids, hydrosalpinx, and male infertility causes:

In another embodiment, the method includes obtaining items of information relating to at least the variables needed to determine the endometrial state as described here above, or more. As such, in other embodiments, the method includes obtaining items of information relating to said variables and at least one more, including 2 or more, 3 or more, 4 or more, 5 or more, 10 or more and the like.

Preferably, in addition to endometrial state and/or uterine receptivity profile, the method includes obtaining items of information of the following group: histological dating (receptivity window determination); endometrium characteristics (such as, for example, endometrial thickness, endometrial volume, endometrial vascularization, uterine artery dopplers); age of the subject; infertility etiology; infertility data such as summary of the previous history and number and quality of transferred embryos; hormonal evaluation of ovarian reserve (AMH, FSH, Antral follicle count); type of ART (IVF, ICSI, IMSI, insemination).

In another embodiment, the method includes assigning a weighted relative importance to each preselected subject variable in relation to other preselected subject variables.

In some embodiments, the comparing includes applying a decision rule. In some embodiments, the data analysis algorithm comprises the use of a classification tree. In other embodiments, the data analysis algorithm is nonparametric, such as using a Wilcoxon Signed Rank Test. In certain embodiments, the data analysis algorithm detects differences in a distribution of feature values. In some embodiments, the data analysis algorithm includes using a multiple additive regression tree. In some embodiments, the data analysis algorithm is a logistic regression.

One approach to analyze this data is to use a classification tree algorithm that searches for patterns and relationships in large datasets. A "classification tree" is a recursive partition to evaluate a female subject for an in vitro fertilization procedure using a series of questions that are designed to accurately place the subject into one of the classes. Each question asks whether a subject's condition satisfies a given predictor, with each answer being used to guide the user down the classification tree until a class into which the subject falls can be determined. As used herein, a "predictor" is the range of values of the features, such as, for example, the uNK or cytokine endometrial environment activity state or the uNK maturation and recruitment state.

As discussed above, evaluation of a female subject for an in vitro fertilization procedure, including determining her uterine receptivity is done by obtaining and comparing items of information from the female subject to a library of known profile patterns known to be indicative of responsiveness to an in vitro fertilization procedure using an algorithm based upon said preselected subject variables. In some embodiments, a subject's evaluation is provided in a report. Thus, in some embodiments, the method further includes a step of preparing or generating a report that includes information(s) regarding the subject's likelihood of successes for an in vitro fertilization procedure and recommendation(s) for a personalized treatment as described here above. For example, a subject method can further include a step of generating or outputting a report providing the results of a subject's evaluation, which report can be provided in the form of an electronic medium (e.g., an electronic display on a computer monitor), or in the form of a tangible medium (e.g., a report printed on paper or other tangible medium). The report may also include information(s) about the testing facility, which information is relevant to the hospital, clinic, or laboratory in which sample gathering and/or data generation was conducted. This information can include one or more details relating to, for example, the name and location of the testing facility, the identity of the lab technician who conducted the assay and/or who entered the input data, the date and time the assay was conducted and/or analyzed, the location where the sample and/or result data is stored, the lot number of the reagents (e.g., kit, etc.) used in the assay, and the like. Said report may also include information(s) relating to the service provider, subject data and sample data.

The interpretive report portion of the report includes information generated after processing of the data as described herein. The interpretive report can include an evaluation of a female subject for an in vitro fertilization procedure. The interpretive report can include, for example, the interpretation of the uterine receptivity based on the data obtained as described above and optionally, recommendation(s) for a personalized treatment for in vitro fertilization.

The methods and systems described herein can be implemented in numerous ways. In one embodiment of particular interest, the methods involve use of a communications infrastructure, for example the internet. Several embodiments of the invention are discussed below. It is also to be understood that the present invention may be implemented in various forms of hardware, software, firmware, processors, or a combination thereof. The methods and systems described herein can be implemented as a combination of hardware and software. The software can be implemented as an application program tangibly embodied on a program storage device, or different portions of the software implemented in the user's computing environment (e.g., as an applet) and on the reviewer's computing environment, where the reviewer may be located at a remote site associated (e.g., at a service provides facility).

The various elements of the computing device, such as the input device, may be associated with other elements of the system via a wired connection or a wireless connection, including, for example, a wireless LAN connection. Bluetooth connection protocol, ZigBee connection protocol, radio-frequency connection protocol, or a cellular phone connection protocol, including code derived multiple access (CDMA) or via a global system for mobile communication (GSM).

The application program for executing the algorithms described herein may be uploaded to, and executed by, a machine comprising any suitable architecture. In general, the machine involves a computer platform having hardware such as one or more central processing units (CPU), a random access memory (RAM), and input/output (I/O) interface(s). The computer platform also includes an operating system and microinstruction code. The various processes and functions described herein may either be part of the microinstruction code or part of the application program (or a combination thereof) which is executed via the operating system. In addition, various other peripheral devices may be connected to the computer platform such as an additional data storage device and a printing device.

Part or all of the input and output data can also be sent electronically; certain output data (e.g., reports) can be sent electronically or telephonically (e.g., by facsimile, e.g., using devices such as fax back). Exemplary output receiving devices can include a display element, a printer, a facsimile device and the like. Electronic forms of transmission and/or display can include email, interactive television, and the like. In an embodiment of particular interest, all or a portion of the input data and/or all or a portion of the output data (e.g., usually at least the final report) are maintained on a web server for access, preferably confidential access, with typical browsers. The data may be accessed or sent to health professionals as desired. The input and output data, including all or a portion of the final report, can be used to populate a subject's medical record which may exist in a confidential database at the healthcare facility.

A system for use in the methods described herein generally includes at least one computer processor (e.g., where the method is carried out in its entirety at a single site) or at least two networked computer processors (e.g., where data is to be input by a user and transmitted to a remote site to a second computer processor for analysis, where the first and second computer processors are connected by a network, e.g., via an intranet or internet). The system can also include a user component(s) for input; and a reviewer component(s) for review of data, generated reports, and manual intervention. Additional components of the system can include a server component(s); and a database(s) for storing data. The computer processors can be processors that are typically found in personal desktop computers (e.g., IBM, Dell, Macintosh), portable computers, mainframes, minicomputers, or other computing devices, such as Smartphone devices, including, for example, an Apple® iPhone® device.

The networked client/server architecture can be selected as desired, and can be, for example, a classic two or three tier client server model. A relational database management system (RDMS), either as part of an application server component or as a separate component (RDB machine) provides the interface to the database.

In one embodiment, the architecture is provided as a database-centric client/server architecture, in which the client application generally requests services from the application server which makes requests to the database (or the database server) to populate the report with the various report elements as required, particularly the interpretive report elements, especially the interpretation text and alerts. The server(s) (e.g., either as part of the application server machine or a separate RDB/relational database machine) responds to the client's requests.

The invention also contemplates a computer-readable storage medium (e.g. CD-ROM, memory key, flash memory card, diskette, etc.) having stored thereon a program which, when executed in a computing environment, provides for implementation of algorithms to carry out all or a portion of the methods of analysis of evaluating a subject for an in vitro fertilization procedure as described herein. Where the computer-readable medium contains a complete program for carrying out the methods described herein, the program includes program instructions for collecting, analyzing and generating output, and generally includes computer readable code devices for interacting with a user as described herein, processing that data in conjunction with analytical information, and generating unique printed or electronic media for that user.

Where the storage medium provides a program which provides for implementation of a portion of the methods described herein (e.g., the user-side aspect of the methods (e.g., data input, report receipt capabilities, etc.)), the program provides for transmission of data input by the user (e.g., via the internet, via an intranet, etc.) to a computing environment at a remote site. Processing or completion of processing of the data is carried out at the remote site to generate a report. After review of the report, and completion of any needed manual intervention, to provide a complete report, the complete report is then transmitted back to the user as an electronic document or printed document (e.g., fax or mailed paper report). The storage medium containing a program according to the invention can be packaged with instructions (e.g., for program installation, use, etc.) recorded on a suitable substrate or a web address where such instructions may be obtained. The computer-readable storage medium can also be provided in combination with one or more reagents for carrying determining subject information data, e.g., material for determining the endometrial state as described here above.

The materials for use in the methods of the present invention are suited for preparation of kits produced in accordance with well known procedures. The invention thus provides kits comprising reagents useful for assaying the expression of genes disclosed herein and for assessing the endometrial state of the subject for example.

For example, a kit can include one or more nucleic acid probes that hybridize specifically to the gene products as described here above, such as CD56, IL-18, IL-6, IL-12, Tweak, IL-15, G-CSF receptor and Fn14.

In some cases, a kit will include, in addition to a probe that hybridizes specifically to the nucleic acid, products as described here above, one or more probes that hybridize specifically to a reference gene product such as RPL-13A, beta-2 microglobulin and tatabox protein TBP. Such probes can be used in determining normalized expression levels of the genes of interest.

The kits may optionally comprise(s) with an identifying description or label or instructions relating to their use in the methods of the present invention. The kits may comprise containers (including microtiter plates suitable for use in an automated implementation of the method), each with one or more of the various reagents (typically in concentrated form) utilized in the methods of the invention, including, for example, pre-fabricated microarrays, buffers, the appropriate nucleotide triphosphates (e.g., dATP, dCTP, dGTP and dTTP; or rATP, rCTP, rGTP and UTP), reverse transcriptase, DNA polymerase, RNA polymerase, and one or more probes and primers of the present invention appropriate length poly(T) or random primers linked to a promoter reactive with the RNA polymerase).

Instructions for the use of mathematical algorithms used to evaluate a female subject for an in vitro fertilization treatment cycle can also be included in a subject kit. In such embodiments, the kits will further include a written or electronic medium, or instructions to access a remote database, as described above, to provide and/or receive information, which generally includes subject information data, in order to carry out the methods as described above.

Figure 1:
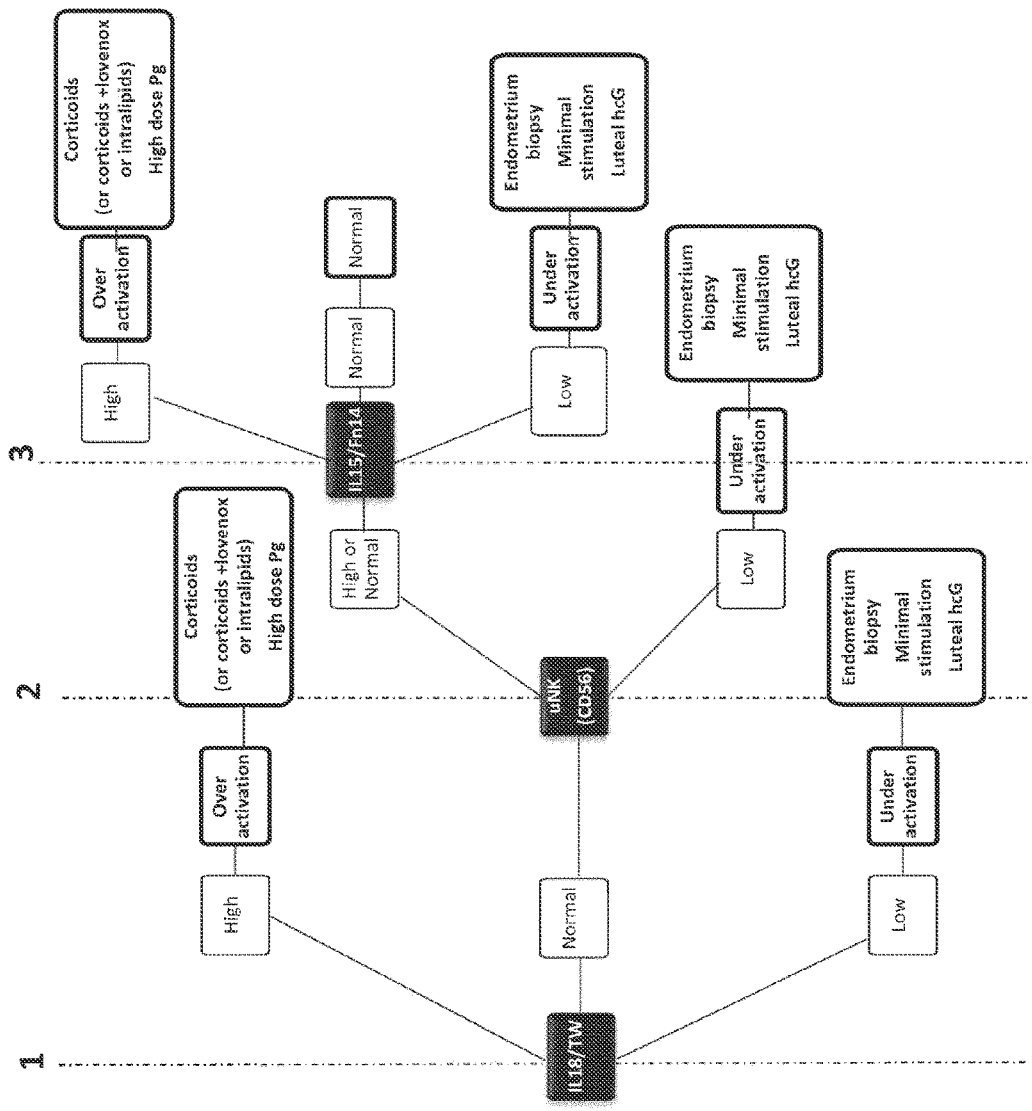
FIG. 1: Expert system for evaluation of uterine receptivity.

The present invention is further illustrated by the following examples.

EXAMPLES

Material and Methods

Subjects with history of previous unexplained and repeated implantation failures were evaluated in the middle luteal phase of a non-conceptual cycle.

Endometrial sampling were performed either:

during a monitored natural cycle 7 to 9 days after the ovulation surge (LH) if the subject had regular cycles, under oestrogen/progestin replacement treatment applied to transfer thawed embryos if cycles are irregular or the subject in amenorhea. Micronized estradiol (Provames, Cassenne, Paris, France) 2 mg is then administrated daily from day 1 to 21, orally and micronized progesterone (Utrogestan; Besins-iscovesco Pharmaceuticals, Paris, France) 200 mg daily, vaginally from days 14 to 21.

Biopsies are performed with a standard Cornier pipette (CCD Laboratories, Paris, France). One portion of the sample is embedded in paraffin for histological dating according to published criteria and for immune staining and enumeration of CD56+ cells (Ventana, 760-2625). The dating and CD56+ immunostaining are performed in order to confirm the middle luteal phase and determine the mean number of uNK/field observed. Another sample is immediately transferred into a RNA Stabilization Solution (RNA Later, QIAGEN, Courtabeuf, France) and immediately stored at −80° C. until later use. The RNA extraction is performed several days later (after confirmation of the luteal phase).

Immunohistochemistry

Sections are cut on a microtome (5 µm thick), placed on SUPERFROST® glass slides (microscope slides from CML, Nemours, France). On the day of experiment the slides are deparaffinated in histolemon and re-hydrated with alcohol. Endogenous peroxydases and biotin activities are inhibited by incubation of the slides in a specific solution (Peroxydase Blocking solution, Dako, Trappes, France and Avidin/Biotin Blocking Vector kit, Abcys, Paris, France). Protein blocking is achieved by a 20 min incubation in PBS (Phosphate Buffer Saline) with 1% of rabbit serum (or goat serum for CD56 staining) and 5% human normal serum (blocking serum). Sections are incubated 1 hour at room temperature with a monoclonal mouse antihuman antibody in case of CD56 staining (Immunotech, Marseille, France). The concentration is 1 µg/mL for anti CD56 antibodies. The antibody is diluted in blocking serum. Between each steps the slides are rinsed three times with PBS. Immunostaining is performed using a secondary antibody, (rabbit anti goat antibody or goat anti mouse from kit Vector ABC, Abcys, Paris, France) for 20 min followed by incubation with a peroxydase-conjugated streptavidin for 30 minutes and then by use of substrate buffer supplemented with liquid DAB and hydrogen peroxide substrate solution (Dako, Trappes, France). Sections are then incubated for 5 minutes with Mayer's haematoxylin (Interchim, Montlucon, France). Finally, the slides are rinsed in distilled water supplemented with 1% of ammoniac water and mounted with Ultramount (Dako, Trappes, France).

For each specimen. CD56+ cells are counted in four 40× fields and then calculated the mean.

Total RNA Extraction and Reverse Transcription

A fragment of each endometrial biopsy is directly disrupted in the lysis buffer of an RNEASY kit (total RNA extraction kit from QIAGEN, Courtabeuf, France) using an ULTRA TURRAX® T15 (hand-held disperser from IKA-WERKE). The total RNA is extracted using the RNEASY kit according to the instruction of the manufacturer. An additional DNase digestion is performed during the extraction process (RNase-free DNase set, QIAGEN, Courtabeuf, France). The RNA integrity and abundance is determined using the Experion system (Experion RNA StdSens kit, Bio-Rad, Hercules, Calif.) and the RNA is stored at −80° C. until final use.

The total RNA (1 µg) is reverse transcribed into cDNA using random primers and Superscript III (Invitrogen, Carlsbad, Calif.) according to the manufacturer's instructions. Controls without reverse transcriptase are systematically performed to detect genomic DNA contamination. The cDNA is stored at −20° C. until further use.

Real Time PCR

Applicant incorporates by reference the ASCII text file filed on Jan. 20, 2015, which has the file name SEQ-LISTING1.txt, was created on Jan. 20, 2015, and is 3.83 KB.

Primer pairs already published as specific for TWEAK (Tweak-S TGCACCTAAAGGCCGGAAAACACG (SEQ ID NO: 1) and Tweak-AS CAGCGCAGGGCCAGCACAC-CATCC (SEQ ID NO: 2)), IL-18 (IL-18-S ATAAAGATG-GCTGCTGAACC (SEQ ID NO: 3) and IL-18-AS TCAAATAGAGGCCGATTTCC (SEQ ID NO: 4)), Beta-2 microglobulin (β2M) (b2M-S TGCTGTCTCCATGTTT-GATGTATCT (SEQ ID NO: 5) and b2M-AS TCTCTGCTC-CCCACCTCTAAGT (SEQ ID NO: 6)), Ribosomal protein L13A (RPL13A) (RPL13A-S CCTGGAGGAGAAGAG-GAAAGAGA (SEQ ID NO: 7) and RPL13-AS TTGAG-GACCTCTGTGTATTTGTCAA (SEQ ID NO: 8)) were designed. Fn14 specific primers (Fn14-S TTTCTG-GCTTTTTGGTCTGG (SEQ ID NO: 9) and Fn14-AS GGCACATTGTCACTGGATCA (SEQ ID NO: 10)), IL-15 (IL-15-S CTAGAGCCAACTGGGTGAATG (SEQ ID NO: 11) and IL-15 AS CATCTCCGGACTCAAGTGAAA (SEQ ID NO: 12)) and G-CSF receptor (G-CSFR-S GTC-CAAGATCACAAAGCTGGT (SEQ ID NO: 13) and G-CSFR-AS CCGCACTCCTCCAGACTTC (SEQ ID NO: 14)) were designed using the Universal Probe Library Assay Design Center (www.roche-applied-science.com). The Fn14, IL-15 and G-CSFR sequences were searched against GenBank sequences with the BLAST program to ensure the specificity of primers.

Real-time PCR is carried out using a LIGHTCYCLER® 480 apparatus (PCR amplification and detection instrument from Roche, Meylan, France). Reactions are set up using the following final concentrations: 0.5 µM of sense and antisense primers, 1× 480 SYBR Green Master mix and 4 µl of 1/20 diluted cDNA. The cycling conditions were as follows: denaturation (95° C. for 5 min), amplification and quantitation (95° C. for 10 s, 60° C. for 10 s and 72° C. for 15 s) repeated 40 times, a melting curve program (65-95° C. with a ramp rate of 2.2° C./s) and a cooling step to 4° C. The assay included a non-template control, a calibrator and each of the test cDNAs. All were carried out in duplicate.

The amplification efficiency was estimated using serial dilutions of each specific amplicons. Data were analysed using LIGHTCYCLER® 480 Relative Quantification software, using the normalisation strategy with the geometric mean of two selected internal controls.

The two internal controls (β2M, RPL13A) used in this study were selected by geNorm program (data not shown). Each specific amplification efficiency was >1.8.

Results 1

Every ninth couple in Europe and USA is affected by implantation disorders and pregnancy wastage and majority of pregnancy losses occur before or during implantation. Therefore, understanding the cross talk between fetal and maternal components before, during and after their confrontations remains a major challenge.

Human implantation may be described as a three steps process starting with the apposition and adhesion of a competent blastocyst to the endometrium epithelium and continuing by an extensive invasion throughout the first trimester of pregnancy in a receptive endometrium. The complex very highly reciprocal orchestrated process of human implantation leads to the essential construction of a haemochorial placenta.

Uterine remodeling events required for a successful pregnancy begin before implantation with the decidualization of the endometrium, which occur even in the absence of a fertilized concept in human. These endometrial modifications define the implantation window and last 5 days—from 4 to 9 days after ovulation- and constitute the receptive endometrium. Human decidualization is characterized by an influx of a distinctive lymphocyte population composed mainly of maternal uterine natural killer cells. Trophoblast invasion is directed by uterine Natural Killer (uNK) cells through an orchestrated and regulated release of cytokines and proangiogenic factors that promote the vascular remodeling.

Decidualization is a vital process for human pregnancy, functioning to provide maternal immune tolerance, protection of the fetus and regulate the placentation. The local environment and its immune equilibrium will be crucial.

From an immune point of view, the implantation window is characterized by a switch of categories of the immune cells. While in the proliferative phase, most of immune cells belong to the adaptative local immunity in order to defend the reproductive tract from infection, in the middle luteal phase most of immune cells belong to the innate immunity. Such switch appears as a fundamental one to allow the phenomenon of local tolerance to the "semiallogenic" fetus.

So at the time of implantation, main immune actors are the uterine natural killers cells (65-70%), the antigen presenting cells as macrophages (10-20%), T regulatory cells (<20%) and dendritic cells (<2%). Uterine NK cells differ from their peripheral counterpart, not only in phenotype but also in apparent function. Uterine NK cells are typically CD56bright/CD16−, while peripheral NKs are CD56dim/

CD16+. CD16 is directly involved in triggering the lysis of target cells. The repertory of activating and inhibiting receptors which regulate the NK related activity are different if compared CD56bright cells originating from blood. The absence of CD16 expression on uNKs results in reduced cytotoxicity in these cells, switching function to cytokine production. However, uterine NK cells are potentially cytotoxic if triggered by a local environment and able to clear virus-infected cells or trophoblastic cells or embryos activated through an excess of pro-inflammatory cytokines.

IL-15 knockout mice are fertile, but they display impaired decidual integrity, unmodified spiral arteries, and lack of uNK at the implantation. IL-15 is directly involved in post-ovulatory uterine recruitment of NK cells. IL-15 is reported to be essential for type 2 cytokine production by the uNK cells. Unlike its effects on blood NK cells, interleukin-15 does not transform the uNK cells into potent cytolytic cells if not present in excess and participated to their maturation. This is critically important for a cell that is present at the maternal fetal interface where cytolytic activity would destroy trophoblast. In human, the mRNA endometrial expression of IL-15 correlates with the local recruitment of uterine NK cells and the local angiogenesis. Moreover, either depletion or an excess of expression has been reported in the mild-luteal endometrium of subjects with history of unexplained implantation failures after IVF-ET. It is therefore reasonable to assume that in the human uterus, IL-15 may play a role in promoting the uNK cell survival and expansion as well as driving their differentiation to a non-cytotoxic phenotype. However, if too much expressed, IL-15 may trigger a local cytotoxicity.

Related to IL-15 endometrial expression, IL-18 alone is a Th-2 promoting cytokine, with positive effect on the crucial destabilization of spiral arteries through an action of the angiopoietin-2. Its main role is the remodeling of the maternal-side of vasculature. However, Interleukin-18 is a bivalent cytokines able to react as a pro-inflammatory Th-1 cytokine in presence of interleukin-12. Costimulated with IL-12, IL-18 enhances the local production of IFN-gamma and TNF and activates uterine NK cells in cytototoxic killer cells, IL-18 is representative of the equilibrium of cytokine within the endometrium, if lacking the preparation of spiral arteries to be invaded is not effective and the implantation fail. In excess, IL-18 behaves as a Th-1 cytokine and will trigger immune surrounding cells to induce a cytotoxic deleterious activity.

Understanding the local function of IL-15 and IL-18 needs to take into account the local expression of immuno-regulators such as TWEAK, that is able to modulate the effects of the cytokines. TWEAK (Tumor necrosis factor like WEAK inducer of apoptosis) triggers multiple cellular responses ranging from proliferation to cell death, including control of angiogenesis. TWEAK has also been described as a partner to TNF (Tumor Necrosis Factor) playing a «Yin and Yang» function in immunity. TWEAK mRNA and protein expression does not show variations through the menstrual cycle. However its basal level of expression influence the IL-18 related uNK recruitment and local cytotoxicity. TWEAK acts on the uNK cells cytotoxicity, induced by IL-18 over-expression, by modifying one of the uNK cells cytotoxic receptor expression, NKp46 hence their activity against the embryo. TWEAK appears as a modulator to avoid endometrial uNK cytotoxicity induced by IL-18 over-expression. IL-18 and TWEAK as two independent proteins possibly acting in synergy to maintain the angiogenic/cytotoxic balance related to uNK cells.

Evaluating the uterine receptivity by determining the endometrial state may thus be of interest for evaluating a female subject for an assisted reproduction technology procedure.

Analysis on 225 subjects led to the following observation:

A method based on evaluating the endometrial state by determining the INK cells activity state using an IL-15/Tweak ratio identifies about 42% of tested women as having a normal endometrial state. However, among said 42%, almost 75% did not actually present a normal endometrial state.

Similarly, a method based on evaluating the endometrial state by determining the uNK cells maturation state using an IL-15/Fn14 ratio identifies about 43% of tested women as having a normal endometrial state. However, among said 43%, almost 75% did not actually present a normal endometrial state.

In addition, a method based on evaluating the endometrial state by determining the uNK cells recruitment state counting the number of CD56+ cells identifies about 47% of tested women as having a normal endometrial state. However, among said 47%, 80% did not actually present a normal endometrial state.

An expert system was then developed to evaluate more accurately the endometrial state of women (FIG. 1).

A personalized recommendation can then be suggested depending on the endometrial state of the subject.

Such procedures has been applied to 255 subjects with a previous history of unexplained implantations failures after IVF/ICSI or recurrent miscarriages unexplained by standard genetic, thrombophilia or auto-immune explorations.

For subjects in implantation failures, the mean range of IVF/ICSI previous attempts was three unsuccessful attempts (range: 1-8) with a mean of 7 embryos transferred (Range: 3-25) without subsequent pregnancy. The mean age was 36 years old.

a—Diagnosis of uterine receptivity profile according to the method as described here above 48.5% (124/255) presented an overactivated endometrium (rejection of the embryo).

35.5% (91/255) presented an underactivated endometrium (no adhesion of the embryo).

15.5% (40/255) presented a normal endometrium.

b—Optimization of the IVF/ICSI Attempt by a Personalization of the Uterine Preparation In such population with previous implantation failures, the ongoing pregnancy rate expected at the next IVF/ICSI attempt is between 15 to 20% embryo transfers. Indeed, in France four attempts (oocyte retrieval) are covered by the social insurance.

We were able to evaluate prospectively the outcome of 75 subjects after determination of their uterine receptivity profile and optimization and personalization of their treatment of in vitro fertilization.

The outcome recorded was:

The pregnancy rate at 5 weeks of amenorrhea (visualization of gestational sac),

The pregnancy rate evaluated at 12 week of amenorrhea (ongoing pregnancy with presence of at least one gestational sac with cardiac activity).

The first subsequent embryo transfer (fresh or frozen-thawed) is followed by the uterine evaluation. The physicians in charge applied the recommendations to optimize the uterine receptivity.

For Said Cohort of 75 Subjects:

38% (28/75) presented an over-activated endometrium (tendency to reject the embryo).

42.6% (32/75) presented an under-activated endometrium (problem of embryo adhesion).

20% (15/75) presented a normal endometrium.

The subjects presenting an over-activated endometrium were recommended to have an IVF attempt:
  With no active uterine intervention the cycle before,
  Corticoids,
  High dose of progesterone in e luteal phase.

The subjects presenting an under-activated endometrium were treated with an endometrial biopsy performed in the middle luteal phase of the cycle preceding the IVF attempt, a minimal ovarian stimulation and an adjunction of chorionic gonadotrophin hormone in the luteal phase after the embryo transfer.

The ongoing pregnancy rate after personalization of the treatment at the first subsequent embryo transfer was:

In case of an overactivated endometrium:
  The pregnancy rate at 5 week of amenorrhea was 46% (13/28).
  The ongoing pregnancy rate at 12 weeks of amenorrhea was 39% (11/28).

In case of underactivated endometrium:
  The pregnancy rate at 5 week of amenorrhea was 53% (17/32).
  The ongoing pregnancy rate at 12 weeks of amenorrhea was 43.7% (14/32).

In case of a normal endometrium:
  The pregnancy rate at 5 week of amenorrhea was 26% (4/15).
  The ongoing pregnancy rate at 12 weeks of amenorrhea was 20% (3/15).

These results suggest that determining the uterine receptivity to optimize it status restitutes an optimal potential of implantation in subjects with previous unexplained implantation failures. Indeed, an ongoing pregnancy around 40% is considered as a good pregnancy rate and is expected in young subject at their first of second IVF/ICSI attempts.

In the present clinical context (third attempt, past of unexplained and repeated implantation failures), the expected pregnancy rate was 20%, the one observed in the group with normal endometrium and probably associated with other trouble related either to the oocyte or to the spermatozoa.

Moreover, the expected rate of miscarriage was over 25% for subject presenting an underactivated or overactivated endometrium.

Following the method as described above, the rate decreased to 10% (5/50) in this high risk group suggesting a control of local deregulations.

Results 2

Correlation of the uterine receptivity profile over two cycles.

We first quantified and normalized the mRNA expression of IL-15, IL-18 among 39 subjects and 37 subjects respectively and the TWEAK mRNA expression among 15 subjects.

The normalized quantifications of the mRNA expression of IL-15, IL-18 and TWEAK were highly and significantly correlated over two cycles.

Figure 2:
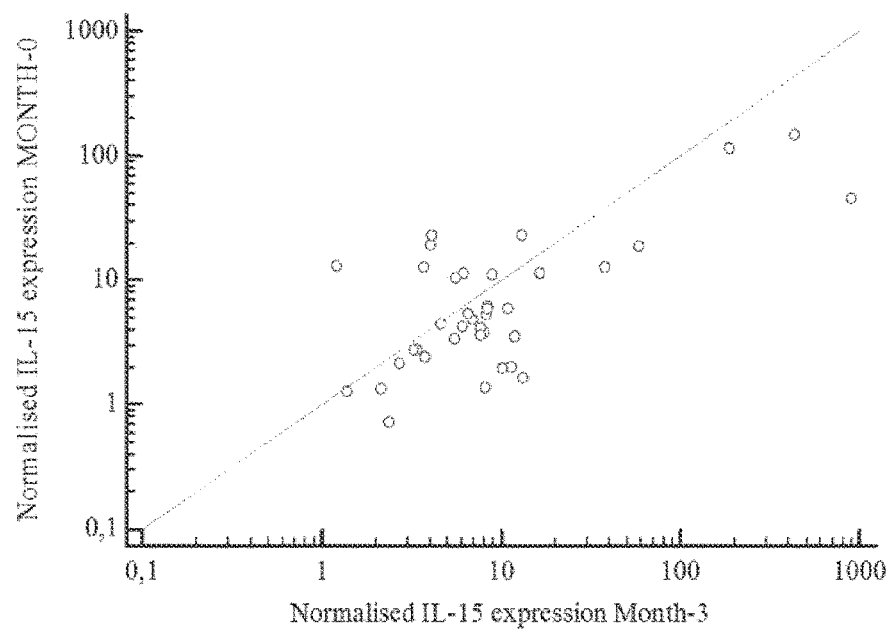
FIG. 2: (A) Correlation of IL-15 mRNA expression over two distinct cycles (n=37 subjects), (B) Correlation of IL-18 mRNA expression over two distinct cycles (n=37 subjects), (C) Correlation of TWEAK mRNA expression over two cycles (n=15 subjects).
Figure 2:
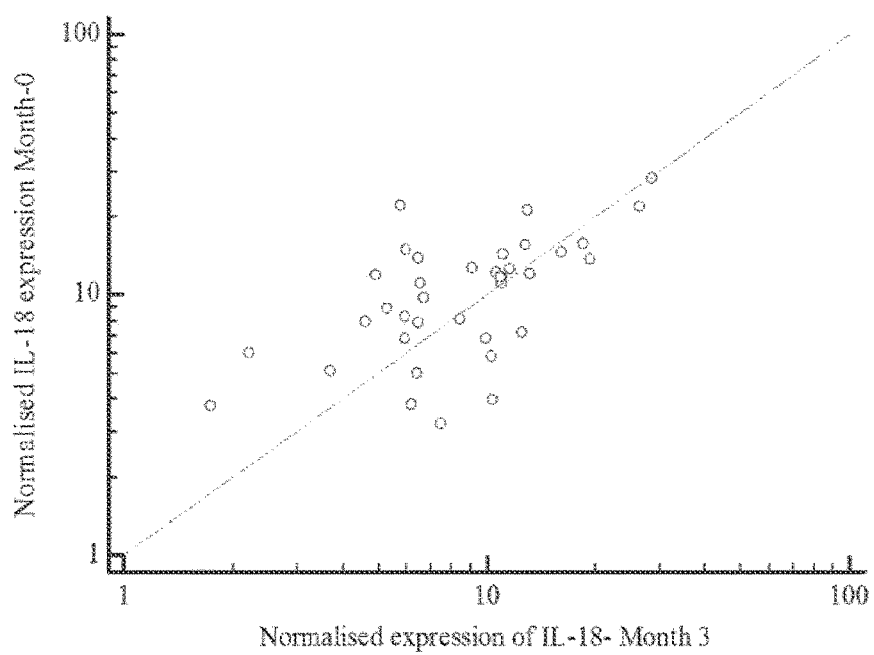
Figure 2:
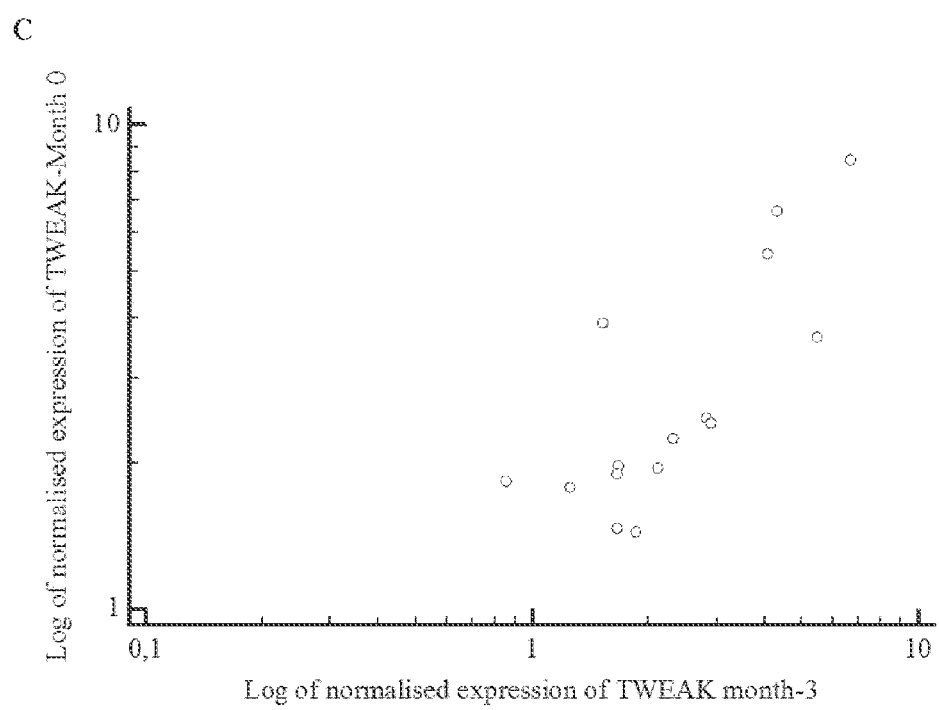

The rank correlation for IL-15 was 0.59 p=0.0001 (FIG. 2A).

The rank correlation for IL-18 was 0.55 p=0.0004 (FIG. 2B).

The rank correlation for TWEAK was 0.72 p=0.0023 (FIG. 2C).

In order to verify that the angiogenic pathways involving IL-18 and its effect on the destabilization of spiral arteries was the same over two cycles, we quantified also among ten subjects the IL-18/TWEAK ratio as well as the angiopoietin-2 normalized expression.

IL-18/TWEAK was highly correlated over two cycles (r=0.77, p=0.01) as well as the angiopietin-2 mRNA expression (r=0.93, p=0.0001) and Tie-2 expression.

Based on these results, we can postulate that exploring a cycle is representative of disorders occurring each cycle. Disorders are related not to the cycle itself but to the immune local profile of the subject.

Results 3

In the context of over-activation, many molecular and immune pathways may be implicated and result at the end is an over-immune activation.

The direct consequence is that the treatment efficient to control the over-immune activation will have to control the specific pathways involved to be effective.

In this context of over-activation, the drug candidates are:
  Corticoids (for their anti-inflammatory effects),
  Low dose heparins (for the control of the complement and anti-thrombotic effects),
  Low dose aspirin (for anti-prostaglandin, anti-thrombotic effect),
  Intralipids (control of Th-1/Th-2 equilibrium).

As the first line of treatment is corticoids in this context, we evaluated among 27 patients during two cycles the immune molecular endometrial profile before and after corticoids.

The response to treatment was either defined by a normalization of the ratio IL-18/Tweak, IL-15/Fn-14 under corticoids or defined by an evolutive pregnancy if no exploration was available under corticoids.

We observed in patients with endometrial over-immune activation an effective response to corticoids in 15/27 (55%).

Figure 3:
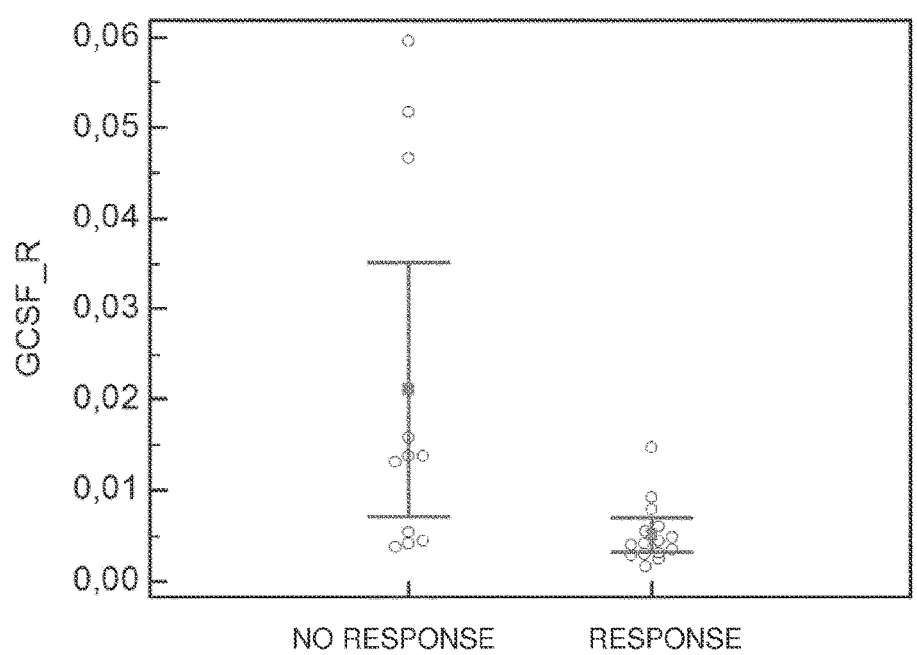
FIG. 3: Correlation of GCSF receptor expression and response to corticoids.

All patients with response to corticoids had a G-CSF Receptor expression below the threshold of 0.7 while all patients with no response had a G-CSF receptor expression over 0.7 (p>0.0001) (FIG. 3).

Results 4

To optimize the potentiality of implantation of patients with history of repeated and unexplained implantation failures after IVF-ET (RIF) accordingly to their immune endometrial profile, a prospective observational Cohort study of 299 RIF patients was performed. A pre-conception immune uterine check-up is performed followed by recommendations of personalized strategies in case of poor or over-endometrial activation. The outcome is the pregnancy rate occurring after the first fresh or thawed embryo transfer following the evaluation.

The endometrial biopsy is performed in the luteal phase of a non-conceptual cycle with a Pipette de Cornier®. On each sample, after histological dating, we quantified the uterine Natural killer cells (uNK) mobilization (immunostaining CD56$^+$), the endometrial mRNA expression of IL-15 (reflecting the maturation state of uNK), of IL-18 (reflecting the Th-1/Th-2 cytokine environment) and of TWEAK/Fn-14 (reflecting the TNF related local immune-regulation) by real time PCR.

The final diagnosis defining the mechanism generating repeated implantation failures was a step by step deduction taking in account in first instance the cytokine immune environment (IL-18/TWEAK) and in a second step the mobilization and maturity of uNK cells.

A low mRNA expression of IL-18/TWEAK with or without low mRNA expression of IL-15/Fn-14 and/or a low uNK cell mobilization defines a poor immune state of activation and a putative mechanism of RTF by insufficient adhesion.

A normal mRNA expression of IL-18/TWEAK with low mRNA expression of IL-15/Fn-14 and/or a low uNK cell mobilization defines a poor immune state of activation and a putative mechanism of RIF by insufficient adhesion.

A high expression of IL-18/TWEAK alone defines an over-activated immune state.

A normal mRNA expression of IL-18/TWEAK with high mRNA expression of IL-15/Fn-14 and/or high uNK cell mobilization defines an over immune state of activation and a putative mechanism of RIF by rejection of the embryo.

In case of poor activation, recommendations were to perform a local injury the cycle preceding the attempt, to apply a minimal ovarian stimulation, to supplement the luteal phase with human Chorionic Gonadotropin and to have sexual intercourse. In the opposite case of over activation, recommendations were no local injury the cycle before, Prednisolone 20 mg and vitamin E from day −1 of the IVF cycle, high dose of progesterone (1200 mg vaginally) with estrogens in the luteal phase and no sexual intercourse.

The mean age of the cohort (37 years old) was taken into account with the mean range of previous attempt (mean of 3 attempts), the mean number of embryos previously transferred (more than 6 embryos) that the expected ongoing pregnancy rate without changing the strategy at the next attempt would be expected to be around 20%.

TABLE 1

Preliminary results on the first 299 outcomes

| Immune uterine Check-up | Poor local activation | Over local activation | Normal activation |
|---|---|---|---|
| Number of RIF Patients | 74 | 155 | 62 |
| Pregnancy rate after treatment of patients having a poor or over local activation | 56.7% (42/74) | 49% (76/155) | 28% (17/62) |
| Ongoing Pregnancy rate after treatment of patients having a poor or over local activation | 52.7% (39/74) | 42% (65/155) | 21% (13/62)** |

Conclusion: On 299 patients who experienced previously repeated implantation failure, the preconception immune evaluation (method of the invention) documented immune uterine deregulations in 77% of the patients. In the group in which endometrial immune deregulation was observed, the optimization of the uterine receptivity accordingly to their immune endometrial profile (by specific treatments) significantly enhanced the subsequent pregnancy rate (see Table 1). Expected ongoing pregnancy rate was about 20%. We then observed a relative increase over 100% between the observed and expected ongoing pregnancy rate when the patients were classified as having a poor or over local activation of the endometrium and then treated accordingly.

Results 5

To determine whether an order among the evaluated parameters is necessary to define the mechanism of implantation failure, patients with successful pregnancy after personalization of their IVF attempt accordingly to their endometrial cytokinic profile were selected. The order of decision applied was to first consider the cytokine immune environment IL-18/TWEAK, then the recruitment and maturity of uNK cells: IL-15/Fn-14 and CD56 cells count.

We then selected patients with high IL-18/TWEAK expression (over-activated state) which were evaluated under corticoids as a first line of treatment with either high or low basal IL-15/Fn-14 expression. Our objective was to analyse subsequent variation on IL-15/Fn-14 under treatment.

Figure 4:
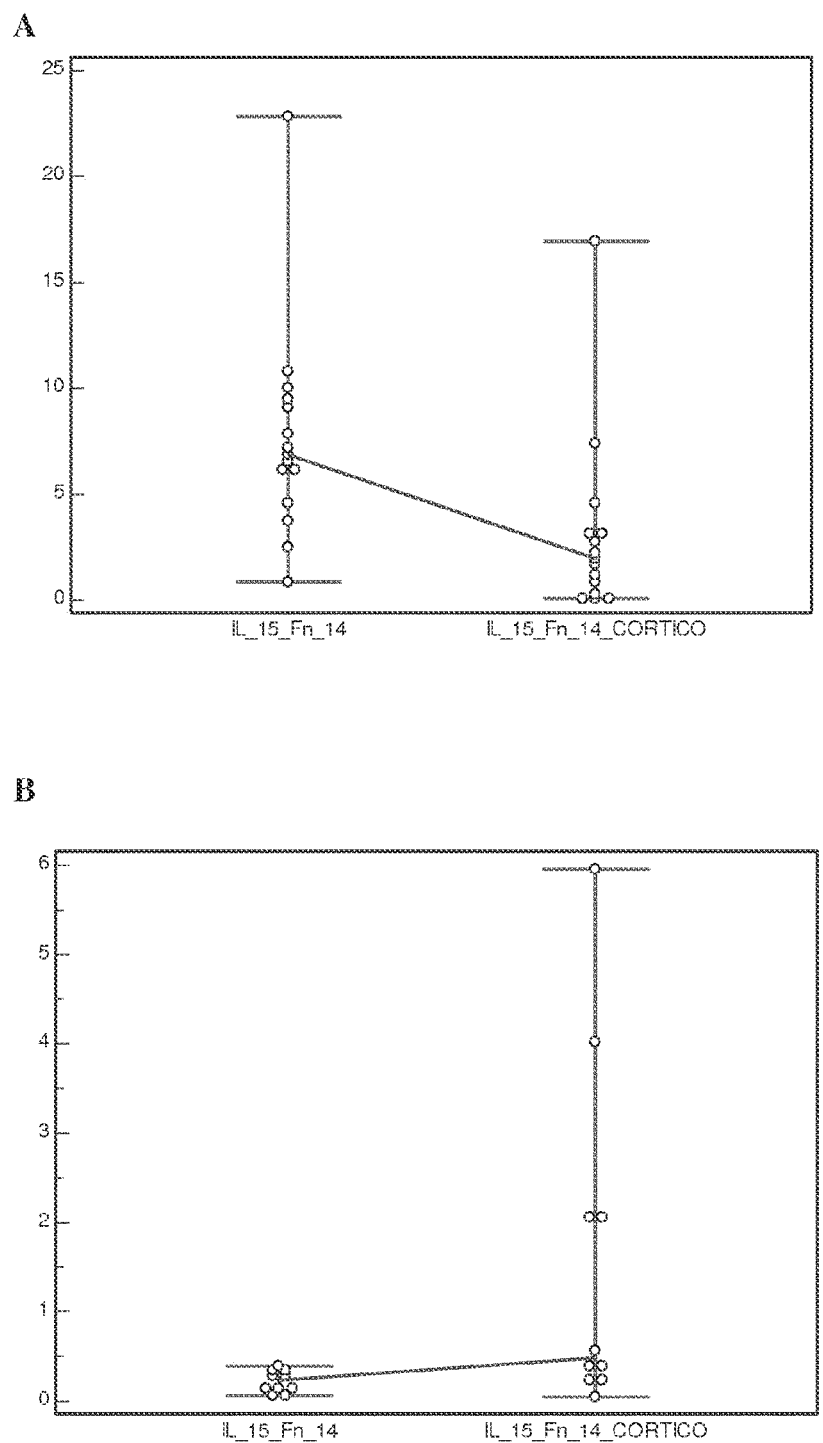
FIG. 4: Evolution of IL-15/Fn-14 before and under corticoids. (A) shows the RNA expression of IL-15/Fn-14 in 14 cases of implantation failures diagnosed with basal both over-expression of IL-18/TWEAK and over-expression of IL-15/Fn-14. (B) shows the mRNA expression of IL-15/Fn-14 for 10 patients with an over-expression of IL-18/TWEAK and a low expression of IL-15/Fn-14

While, a significant decrease is observed when basal IL-15/Fn-14 expression is high or normal (>3) (FIG. 4A). Over the 10 samples with basal low IL-15/Fn-14 expression (FIG. 4B), a normalization of the IL-15/Fn-14 ratio is observed in 5 cases and a paradoxical response was observed with as consequence an hyper-expression in two cases. This could be consecutive to the action of corticoids on the transcription of IL-15 itself. Indeed, a cortico-releasing element is present in the sequence of IL-15. So in these cases of II mRNA low expression in cytotoxic environment, the stimulation of the CRE by corticoids disrupts the local regulation, IL-18/TWEAK expression should be first considered to personalize subsequent treatment. Therefore, IL-15/Fn-14 expression should be considered in second step if IL-18/TWEAK is normal.

Moreover, 109 cases of successful pregnancy were retrospectively analyzed, the mRNA expression of IL-15/Fn-14 with the CD56 mobilization was determined in a first step followed by IL-18/TWEAK. In 12 cases over 109, mRNA expression of IL-15/Fn-14 was low (corresponding to an immature uNK state) while IL-18/TWEAK was high suggesting excess of Th-1 cytokines in the endometrial environment. If IL-15/Fn-14 had been considered in first hand, it would have led to the opposite diagnosis and personalization.

In 4 cases over 109, mRNA expression of IL-15/Fn-14 was high (suggesting a hyper-activated uNK state) while IL-18/TWEAK was low suggesting the opposite: a depletion of Th-2 cytokines in the endometrial environment. If IL-15/Fn-14 would have been considered first, we would have deducted the opposite diagnosis.

In total, we would have deduced a wrong endometrial state and a wrong treatment in 14% of the cases. IL-18/TWEAK reflecting the cytokine immune environment of the overall endometrium and the cytokine environment of all the immune cells (including T regulatory and dendritic cells) should be considered before the recruitment and maturity of uNK cells (see FIG. 1).

The invention claimed is:

1. A method for providing an adapted assisted reproduction technology (ART) procedure to a female subject, comprising:
   determining a uterine receptivity profile of said female subject during a uterine implantation window by determining on an endometrial sample of said female subject an endometrial state by:
   a) measuring expression levels of IL-18 and Tweak, calculating an IL-18/Tweak ratio value, and comparing the calculated IL-18/Tweak ratio value to a reference value from a fertile female subject;
   b) measuring expression levels of IL-15 and Fn14, calculating an IL-15/Fn14 ratio value and comparing the calculated IL-15/Fn14 ratio value to a reference value from a fertile female subject;
   c) measuring a number of CD56+ uterine NK (uNK) cells or expression level of CD56 and comparing the measured number or expression level to a reference value from a fertile female subject; and
   d) identifying the female subject as having an under-activated endometrial state or an over-activated endometrial state based on the comparing of the calculated IL-18/Tweak ratio value and the reference value, the comparing of the calculated IL-15/Fn14 ratio value and the reference value, and the comparing of the measured number of CD56+ uNK cells or expression level of CD56 and the reference value, wherein an under-activated endometrial state is indicative of the female subject having an inappropriate uterine receptivity profile due to an absence of receptivity, and an over-activated endometrial state is indicative of the female subject having an inappropriate uterine receptivity profile due to an abnormal receptivity; and
providing an ART procedure adapted to the endometrial state of the female subject, wherein:
(i) the ART procedure for said female subject having an under-activated endometrial state indicative of an inappropriate uterine receptivity profile due to an absence of receptivity comprises at least one step selected from the group consisting of:
stimulating mechanically luteal phase endometrium prior to an in vitro fertilization (IVF) cycle;
decreasing hormone stimulation during an IVF cycle by administering a number of follicle-stimulating hormone (FSH) units to trigger an ovulation so that oestradiol levels measured in a blood sample on the day ovulation is triggered are lower than 1,500 pg/ml;
decreasing hormone stimulation during an IVF cycle by transferring, after thawing, a previously frozen embryo in a monitored natural IVF cycle rather than in an IVF cycle substituted with an administration of oestrogens and progesterone; and
administering human Chorionic Gonadotropin (hCG) hormone during the implantation window; and
(ii) the ART procedure for said female subject having an over-activated endometrial state indicative of an inappropriate uterine receptivity profile due to an abnormal receptivity comprises at least one step selected from the group consisting of:
administering a high level of ovarian stimulation during an IVF cycle by administering 225 to 400 IU of follicle-stimulating hormone (FSH) to trigger a superovulation;
administering a high level of ovarian stimulation during an IVF cycle by transferring, after thawing, a previously frozen embryo in an IVF cycle substituted with an administration of oestrogens and progesterone;
administering a high level of ovarian stimulation during an IVF cycle by administering oestradiol in the luteal phase after embryo transfer;
administering progesterone at 1,200 mg/day in the luteal phase;
administering a hormonal stimulation and administering a drug aiming at controlling a pro-inflammatory local environment from the beginning of the hormonal stimulation, said drug being selected from the group consisting of corticosteroids, a combination of low dose of acetyl salicylic acid with low-weight heparins, and intralipids;
administering a therapeutically effective amount of antioxidant agent; and
administering a corticoid being prednisolone and an antioxidant agent being vitamin E from the day before an IVF cycle.

2. The method according to claim 1, wherein the female subject has an under-activated endometrial state indicative of an inappropriate uterine receptivity profile due to an absence of receptivity, and wherein the adapted ART procedure comprises:
stimulating mechanically luteal phase endometrium prior to an in vitro fertilization (IVF) cycle, wherein said mechanical stimulation comprises performing a local injury the cycle preceding an in vitro fertilization attempt.

3. The method according to claim 1, wherein a female subject with a lower IL-18/Tweak ratio value as compared to the reference value, and
with or without a lower IL-15/Fn14 ratio value as compared to the reference value, or
with or without a lower number of CD56+ uNK cells or lower level of CD56 expression as compared to the reference value, or
with or without both a lower IL-15/Fn14 ratio value and a lower number of CD56+ uNK cells or lower level of CD56 expression as compared to the reference value,
has an under-activated endometrial state indicative of an inappropriate uterine receptivity profile due to an absence of receptivity.

4. The method according to claim 1, wherein a female subject with a normal IL-18/Tweak ratio value as compared to the reference value, and
with a lower IL-15/Fn14 ratio value as compared to the reference value, or
with a lower number of CD56+ uNK cells or lower level of CD56 expression as compared to the reference value, or
with both a lower IL-15/Fn14 ratio value and a lower number of CD56+ uNK cells or lower level of CD56 expression as compared to the reference value,
has an under-activated endometrial state indicative of an inappropriate uterine receptivity profile due to an absence of receptivity.

5. The method according to claim 1, wherein a female subject with a normal IL-18/Tweak ratio value as compared to the reference value, and
with a normal or higher number of CD56+ uNK cells or normal or higher level of CD56 expression as compared to the reference value, and
with a lower IL-15/Fn14 ratio value as compared to the reference value,
has an under-activated endometrial state indicative of an inappropriate uterine receptivity profile due to an absence of receptivity.

6. The method according to claim 1, wherein a female subject with a normal IL-18/Tweak ratio value as compared to the reference value, and
with a normal or higher number of CD56+ uNK cells or normal or higher level of CD56 expression as compared to the reference value, and
with a higher IL-15/Fn14 ratio value as compared to the reference value,
has an over-activated endometrial state indicative of an inappropriate uterine receptivity profile due to an abnormal receptivity.

7. The method according to claim 1, wherein a female subject with a higher IL-18/Tweak ratio value as compared to the reference value, and
with or without a higher IL-15/Fn14 ratio value as compared to the reference value, or
with or without a higher number of CD56+ uNK cells or higher level of CD56 expression as compared to the reference value, or
with or without both a higher IL-15/Fn14 ratio value and a higher number of CD56+ uNK cells or higher level of CD56 expression as compared to the reference value, has an over-activated endometrial state indicative of an inappropriate uterine receptivity profile due to an abnormal receptivity.

* * * * *

SEQUENCE LISTING

<160> NUMBER OF SEQ ID NOS: 14

<210> SEQ ID NO 1
<211> LENGTH: 24
<212> TYPE: DNA
<213> ORGANISM: artificial sequences

```
<220> FEATURE:
<221> NAME/KEY: source
<222> LOCATION: 1..24
<223> OTHER INFORMATION: /mol_type = DNA
      /note =Tweak-S
      /organism = artificial sequences

<400> SEQUENCE: 1
tgcacctaaa ggccggaaaa cacg                                          24

<210> SEQ ID NO 2
<211> LENGTH: 24
<212> TYPE: DNA
<213> ORGANISM: artificial sequences
<220> FEATURE:
<221> NAME/KEY: source
<222> LOCATION: 1..24
<223> OTHER INFORMATION: /mol_type=DNA
      /note=Tweak-AS
      /organism=artificial sequences

<400> SEQUENCE: 2
cagcgcaggg ccagcacacc atcc                                          24

<210> SEQ ID NO 3
<211> LENGTH: 20
<212> TYPE: DNA
<213> ORGANISM: artificial sequences
<220> FEATURE:
<221> NAME/KEY: source
<222> LOCATION: 1..20
<223> OTHER INFORMATION: /mol_type=DNA
      /note = IL-18-S
      /organism=artificial sequences

<400> SEQUENCE: 3
ataaagatgg ctgctgaacc                                               20

<210> SEQ ID NO 4
<211> LENGTH: 20
<212> TYPE: DNA
<213> ORGANISM: artificial sequences
<220> FEATURE:
<221> NAME/KEY: source
<222> LOCATION: 1..20
<223> OTHER INFORMATION: /mol_type=DNA
      /note=IL-18-AS
      /organism=artificial sequences

<400> SEQUENCE: 4
tcaaatagag gccgatttcc                                               20

<210> SEQ ID NO 5
<211> LENGTH: 25
<212> TYPE: DNA
<213> ORGANISM: artificial sequences
<220> FEATURE:
<221> NAME/KEY: source
<222> LOCATION: 1..25
<223> OTHER INFORMATION: /mol_type=DNA
      /note=b2M-S
      /organism=artificial sequences

<400> SEQUENCE: 5
tgctgtctcc atgtttgatg tatct                                         25

<210> SEQ ID NO 6
<211> LENGTH: 22
<212> TYPE: DNA
```

```
<213> ORGANISM: artificial sequences
<220> FEATURE:
<221> NAME/KEY: source
<222> LOCATION: 1..22
<223> OTHER INFORMATION: /mol_type=DNA
      /note=b2M-AS
      /organism=artificial sequences

<400> SEQUENCE: 6
tctctgctcc ccacctctaa gt                                              22

<210> SEQ ID NO 7
<211> LENGTH: 23
<212> TYPE: DNA
<213> ORGANISM: artificial sequences
<220> FEATURE:
<221> NAME/KEY: source
<222> LOCATION: 1..23
<223> OTHER INFORMATION: /mol_type=DNA
      /note=RPL13A-S
      /organism=artificial sequences

<400> SEQUENCE: 7
cctggaggag aagaggaaag aga                                             23

<210> SEQ ID NO 8
<211> LENGTH: 25
<212> TYPE: DNA
<213> ORGANISM: artificial sequences
<220> FEATURE:
<221> NAME/KEY: source
<222> LOCATION: 1..25
<223> OTHER INFORMATION: /mol_type=DNA
      /note=RPL13A-AS
      /organism=artificial sequences

<400> SEQUENCE: 8
ttgaggacct ctgtgtattt gtcaa                                           25

<210> SEQ ID NO 9
<211> LENGTH: 20
<212> TYPE: DNA
<213> ORGANISM: artificial sequences
<220> FEATURE:
<221> NAME/KEY: source
<222> LOCATION: 1..20
<223> OTHER INFORMATION: /mol_type=DNA
      /note=Fn14-S
      /organism=artificial sequences

<400> SEQUENCE: 9
tttctggctt tttggtctgg                                                 20

<210> SEQ ID NO 10
<211> LENGTH: 20
<212> TYPE: DNA
<213> ORGANISM: artificial sequences
<220> FEATURE:
<221> NAME/KEY: source
<222> LOCATION: 1..20
<223> OTHER INFORMATION: /mol_type=DNA
      /note=Fn14-AS
      /organism=artificial sequences

<400> SEQUENCE: 10
ggcacattgt cactggatca                                                 20

<210> SEQ ID NO 11
<211> LENGTH: 21
```

```
<212> TYPE: DNA
<213> ORGANISM: artificial sequences
<220> FEATURE:
<221> NAME/KEY: source
<222> LOCATION: 1..21
<223> OTHER INFORMATION: /mol_type=DNA
      /note=IL-15-S
      /organism=artificial sequences

<400> SEQUENCE: 11
ctagagccaa ctgggtgaat g                                              21

<210> SEQ ID NO 12
<211> LENGTH: 21
<212> TYPE: DNA
<213> ORGANISM: artificial sequences
<220> FEATURE:
<221> NAME/KEY: source
<222> LOCATION: 1..21
<223> OTHER INFORMATION: /mol_type=DNA
      /note=IL-15-AS
      /organism=artificial sequences

<400> SEQUENCE: 12
catctccgga ctcaagtgaa a                                              21

<210> SEQ ID NO 13
<211> LENGTH: 21
<212> TYPE: DNA
<213> ORGANISM: artificial sequences
<220> FEATURE:
<221> NAME/KEY: source
<222> LOCATION: 1..21
<223> OTHER INFORMATION: /mol_type=DNA
      /note = G-CSFR-S
      /organism = artificial sequences

<400> SEQUENCE: 13
gtccaagatc acaaagctgg t                                              21

<210> SEQ ID NO 14
<211> LENGTH: 19
<212> TYPE: DNA
<213> ORGANISM: artificial sequences
<220> FEATURE:
<221> NAME/KEY: source
<222> LOCATION: 1..19
<223> OTHER INFORMATION: /mol_type=DNA
      /note=G-CSFR-AS
      /organism=artificial sequences

<400> SEQUENCE: 14
ccgcactcct ccagacttc                                                 19
```